(12) United States Patent
Shafer

(10) Patent No.: US 8,673,570 B2
(45) Date of Patent: Mar. 18, 2014

(54) SYSTEM AND METHODS TO QUANTIFY AND AMPLIFY BOTH SIGNALING AND PROBES FOR CDNA CHIPS AND GENE EXPRESSION MICROARRAYS

(75) Inventor: David A. Shafer, Atlanta, GA (US)

(73) Assignee: Genetag Technology, Inc., Atlanta, GA (US)

( * ) Notice: Subject to any disclaimer, the term of this patent is extended or adjusted under 35 U.S.C. 154(b) by 0 days.

(21) Appl. No.: 13/403,012

(22) Filed: Feb. 23, 2012

(65) Prior Publication Data

US 2012/0157343 A1 Jun. 21, 2012

Related U.S. Application Data

(63) Continuation of application No. 12/334,036, filed on Dec. 12, 2008, now abandoned, which is a continuation of application No. 10/380,596, filed as application No. PCT/US01/07508 on Mar. 9, 2001, now Pat. No. 7,482,443.

(60) Provisional application No. 60/187,982, filed on Mar. 9, 2000.

(51) Int. Cl.
*C12Q 1/68* (2006.01)
*C07H 21/04* (2006.01)

(52) U.S. Cl.
USPC ........................................ 435/6.12; 536/24.2

(58) Field of Classification Search
None
See application file for complete search history.

(56) References Cited

U.S. PATENT DOCUMENTS 5,629,177 A * 5/1997 Hyman .................. 435/91.2
5,932,451 A * 8/1999 Wang et al. ............ 435/91.21
5,962,272 A * 10/1999 Chenchik et al. ........ 435/91.1
6,509,157 B1 * 1/2003 Martinez .................. 435/6.12

FOREIGN PATENT DOCUMENTS

WO WO 0004192 A1 * 1/2000

OTHER PUBLICATIONS

Spickofsky (A highly efficient directional cDNA cloning method utilizing an asymmetrically tailed linker-primer plasmid, Nucleic Acids Research, vol. 19, No. 25 7105-7111).*

\* cited by examiner

*Primary Examiner* — Christopher M Babic
*Assistant Examiner* — Aaron Priest
(74) *Attorney, Agent, or Firm* — Thomas|Horstemeyer, LLP

(57) ABSTRACT

The invention provides a series of reagent compositions and methods for making and amplifying novel cDNA based probe sets from RNA samples to improve analysis with gene expression arrays. The methods globally produce probe sets with common universal linkers at one or both ends, called WRAP-Probes, wherein the linkers do not bind to the target sequences and they can efficiently bind added reporters to the probes. The universal linkers are also designed as primer binding sites for copying and amplifying the probes, either linearly with one linker, or exponentially with double linkers. The capacity to globally and exponentially amplify the probe set by PCR is a primary advantage. Adding reporters by terminal linkers also improves quantification since each probe gets equivalent signaling. The invention allows expression analysis of small research, clinical and forensic samples to enable improved diagnostics, drug discovery, therapeutic monitoring, and medical, agricultural and general research.

42 Claims, 8 Drawing Sheets

SEQUENCE LISTING

<160> NUMBER OF SEQ ID NOS: 31

<210> SEQ ID NO 1
<211> LENGTH: 27
<212> TYPE: DNA
<213> ORGANISM: Artificial sequence
<220> FEATURE:
<223> OTHER INFORMATION: Nucleotide sequence of a red universal linker

<400> SEQUENCE: 1
ctacgatacg atagcgccta agagtag                                       27

<210> SEQ ID NO 2
<211> LENGTH: 27
<212> TYPE: DNA
<213> ORGANISM: Artificial sequence
<220> FEATURE:
<223> OTHER INFORMATION: Nucleotide sequence of a blue universal linker

<400> SEQUENCE: 2
cctagaccta cgacataggt accctac                                       27

<210> SEQ ID NO 3
<211> LENGTH: 27
<212> TYPE: DNA
<213> ORGANISM: Artificial sequence
<220> FEATURE:
<223> OTHER INFORMATION: Nucleotide sequence of a green universal linker

<400> SEQUENCE: 3
cgtagaacta gcacgctacg tactagg                                       27

<210> SEQ ID NO 4
<211> LENGTH: 27
<212> TYPE: DNA
<213> ORGANISM: Artificial sequence
<220> FEATURE:
<223> OTHER INFORMATION: Nucleotide sequence of a orange universal
      linker

<400> SEQUENCE: 4
ggctatcgct acgtagacta gacctac                                       27

<210> SEQ ID NO 5
<211> LENGTH: 17
<212> TYPE: DNA
<213> ORGANISM: Artificial sequence
<220> FEATURE:
<223> OTHER INFORMATION: Modified poly-T primer; v=a, c, or g at
      position 16; n=a, c, g, or t at position 17
<220> FEATURE:
<221> NAME/KEY: random base
<222> LOCATION: (16)..(17)
<220> FEATURE:
<221> NAME/KEY: misc_feature
<222> LOCATION: (17)..(17)
<223> OTHER INFORMATION: n is a, c, g, or t

<400> SEQUENCE: 5
tttttttttt tttttvn                                                  17

<210> SEQ ID NO 6
<211> LENGTH: 27
<212> TYPE: DNA
<213> ORGANISM: Artificial sequence
<220> FEATURE:
<223> OTHER INFORMATION: Nucleotide sequence of a blue universal linker -continued

<400> SEQUENCE: 6
cctagtacgt agcgtgctag ttctacg                                              27

<210> SEQ ID NO 7
<211> LENGTH: 27
<212> TYPE: DNA
<213> ORGANISM: Artificial sequence
<220> FEATURE:
<223> OTHER INFORMATION: Nucleotide sequence of a orange universal
      linker

<400> SEQUENCE: 7
gtaggtctag tctacgtagc gatagcc                                              27

<210> SEQ ID NO 8
<211> LENGTH: 42
<212> TYPE: DNA
<213> ORGANISM: Artificial sequence
<220> FEATURE:
<223> OTHER INFORMATION: Nucleotide sequence of a red universal linker
      modified with a poly-T primer

<400> SEQUENCE: 8
ctacgatacg atagggccta agagtagttt tttttttttt tt                             42

<210> SEQ ID NO 9
<211> LENGTH: 42
<212> TYPE: DNA
<213> ORGANISM: Artificial sequence
<220> FEATURE:
<223> OTHER INFORMATION: Nucleotide sequence of a green universal linker
      modified with a poly-T primer

<400> SEQUENCE: 9
gcctagacct aggggtagct aggctacttt tttttttttt tt                             42

<210> SEQ ID NO 10
<211> LENGTH: 27
<212> TYPE: DNA
<213> ORGANISM: Artificial sequence
<220> FEATURE:
<223> OTHER INFORMATION: Proximal spacer oligomer RR-SPC-F
<220> FEATURE:
<221> NAME/KEY: Primer
<222> LOCATION: (1)..(27)

<400> SEQUENCE: 10
ctactcttag gccctatcgt atcgtag                                              27

<210> SEQ ID NO 11
<211> LENGTH: 22
<212> TYPE: DNA
<213> ORGANISM: Artificial sequence
<220> FEATURE:
<223> OTHER INFORMATION: Proximal spacer oligomer RR-SPC-F
<220> FEATURE:
<221> NAME/KEY: Primer
<222> LOCATION: (1)..(22)

<400> SEQUENCE: 11
ccagggtttt cccagtcacg ac                                                   22

<210> SEQ ID NO 12
<211> LENGTH: 27
<212> TYPE: DNA
<213> ORGANISM: Artificial sequence
<220> FEATURE:

```
<223> OTHER INFORMATION: Distal spacer oligomer GR-SPC-F
<220> FEATURE:
<221> NAME/KEY: Primer
<222> LOCATION: (1)..(27)

<400> SEQUENCE: 12
gcctagacct aggggtagct aggctac                                            27

<210> SEQ ID NO 13
<211> LENGTH: 24
<212> TYPE: DNA
<213> ORGANISM: Artificial sequence
<220> FEATURE:
<223> OTHER INFORMATION: Distal spacer oligomer GR-SPC-F
<220> FEATURE:
<221> NAME/KEY: Primer
<222> LOCATION: (1)..(22)
<220> FEATURE:
<221> NAME/KEY: Primer
<222> LOCATION: (1)..(24)

<400> SEQUENCE: 13
gagcggataa caatttcaca cagg                                               24

<210> SEQ ID NO 14
<211> LENGTH: 27
<212> TYPE: DNA
<213> ORGANISM: Artificial sequence
<220> FEATURE:
<223> OTHER INFORMATION: Proximal spacer oligomer GR-SPC-F
<220> FEATURE:
<221> NAME/KEY: Primer
<222> LOCATION: (1)..(27)

<400> SEQUENCE: 14
gtagcctagc tacccctagg tctaggc                                            27

<210> SEQ ID NO 15
<211> LENGTH: 27
<212> TYPE: DNA
<213> ORGANISM: Artificial sequence
<220> FEATURE:
<223> OTHER INFORMATION: Distal spacer oligomer RR-SPC-R
<220> FEATURE:
<221> NAME/KEY: Primer
<222> LOCATION: (1)..(27)

<400> SEQUENCE: 15
ctacgatacg atagggccta agagtag                                            27

<210> SEQ ID NO 16
<211> LENGTH: 20
<212> TYPE: DNA
<213> ORGANISM: Artificial sequence
<220> FEATURE:
<223> OTHER INFORMATION: Modified RT primer
<220> FEATURE:
<221> NAME/KEY: Primer
<222> LOCATION: (1)..(20)

<400> SEQUENCE: 16
cgactaccta tctacttttt                                                    20

<210> SEQ ID NO 17
<211> LENGTH: 31
<212> TYPE: DNA
<213> ORGANISM: Artificial sequence
<220> FEATURE:
<223> OTHER INFORMATION: Nucleotide sequence of a first-red primer with
      GeneTAG adapter part 1
```

-continued

<400> SEQUENCE: 17
ctacgatacg atagggccta agagtagcat g                                    31

<210> SEQ ID NO 18
<211> LENGTH: 27
<212> TYPE: DNA
<213> ORGANISM: Artificial sequence
<220> FEATURE:
<223> OTHER INFORMATION: Nucleotide sequence of a first-red primer with
      GeneTAG adapter part 2

<400> SEQUENCE: 18
ctactcttag gccctatcgt atcgtag                                         27

<210> SEQ ID NO 19
<211> LENGTH: 42
<212> TYPE: DNA
<213> ORGANISM: Artificial sequence
<220> FEATURE:
<223> OTHER INFORMATION: Nucleotide sequence of an overlap linker

<400> SEQUENCE: 19
ctacgatacg atagggccta agagtagcga ctacctatct ac                        42

<210> SEQ ID NO 20
<211> LENGTH: 27
<212> TYPE: DNA
<213> ORGANISM: Artificial sequence
<220> FEATURE:
<223> OTHER INFORMATION: Nucleotide sequence of a GeneTAG first-red
      primer

<400> SEQUENCE: 20
ctacgatacg atagggccta agagtag                                         27

<210> SEQ ID NO 21
<211> LENGTH: 31
<212> TYPE: DNA
<213> ORGANISM: Artificial sequence
<220> FEATURE:
<223> OTHER INFORMATION: Nucleotide sequence of a first-green primer
      with specific adapter part 1

<400> SEQUENCE: 21
gcctagacct aggggtagct aggctaccat g                                    31

<210> SEQ ID NO 22
<211> LENGTH: 27
<212> TYPE: DNA
<213> ORGANISM: Artificial sequence
<220> FEATURE:
<223> OTHER INFORMATION: Nucleotide sequence of a first-green primer
      with specific adapter part 2

<400> SEQUENCE: 22
gtagcctagc tacccctagg tctaggc                                         27

<210> SEQ ID NO 23
<211> LENGTH: 27
<212> TYPE: DNA
<213> ORGANISM: Artificial sequence
<220> FEATURE:
<223> OTHER INFORMATION: Nucleotide sequence of a red universal linker

<400> SEQUENCE: 23
gcctagacct aggggtagct aggctac                                         27

<210> SEQ ID NO 24
<211> LENGTH: 27
<212> TYPE: DNA
<213> ORGANISM: Artificial sequence
<220> FEATURE:
<223> OTHER INFORMATION: Nucleotide sequence of a GeneTAG first-green
      primer

<400> SEQUENCE: 24
ctacgatacg atagggccta agagtag                                        27

<210> SEQ ID NO 25
<211> LENGTH: 27
<212> TYPE: DNA
<213> ORGANISM: Artificial sequence
<220> FEATURE:
<223> OTHER INFORMATION: Nucleotide sequence of a ChipTAG first-red
      primer

<400> SEQUENCE: 25
gcctagacct aggggtagct aggctac                                        27

<210> SEQ ID NO 26
<211> LENGTH: 36
<212> TYPE: DNA
<213> ORGANISM: Artificial sequence
<220> FEATURE:
<223> OTHER INFORMATION: Nucleotide sequence of a first-green GeneTAG
      random end linker; n=a, c, g, or t
<220> FEATURE:
<221> NAME/KEY: randombase
<222> LOCATION: (28)..(36)
<220> FEATURE:
<221> NAME/KEY: misc_feature
<222> LOCATION: (28)..(36)
<223> OTHER INFORMATION: n is a, c, g, or t

<400> SEQUENCE: 26
gcctagacct aggggtagct aggctacnnn nnnnnn                              36

<210> SEQ ID NO 27
<211> LENGTH: 36
<212> TYPE: DNA
<213> ORGANISM: Artificial sequence
<220> FEATURE:
<223> OTHER INFORMATION: Nucleotide sequence of a first-red GeneTAG
      random end linker; n=a, c, g, or t
<220> FEATURE:
<221> NAME/KEY: random base
<222> LOCATION: (28)..(36)
<220> FEATURE:
<221> NAME/KEY: misc_feature
<222> LOCATION: (28)..(36)
<223> OTHER INFORMATION: n is a, c, g, or t

<400> SEQUENCE: 27
ctacgatacg atagggccta agagtagnnn nnnnnn                              36

<210> SEQ ID NO 28
<211> LENGTH: 29
<212> TYPE: DNA
<213> ORGANISM: Artificial sequence
<220> FEATURE:
<223> OTHER INFORMATION: Nucleotide sequence of a first-green random
      adaptor part 1; n=a, c, g, or t
<220> FEATURE:
<221> NAME/KEY: random base
<222> LOCATION: (28)..(29)
<220> FEATURE:
<221> NAME/KEY: misc_feature

```
<222> LOCATION: (28)..(29)
<223> OTHER INFORMATION: n is a, c, g, or t

<400> SEQUENCE: 28
gcctagacct aggggtagct aggctacnn                                    29

<210> SEQ ID NO 29
<211> LENGTH: 27
<212> TYPE: DNA
<213> ORGANISM: Artificial sequence
<220> FEATURE:
<223> OTHER INFORMATION: Nucleotide sequence of a first-green random
      adaptor part 2

<400> SEQUENCE: 29
gtagcctagc tacccctagg tctaggc                                      27

<210> SEQ ID NO 30
<211> LENGTH: 29
<212> TYPE: DNA
<213> ORGANISM: Artificial sequence
<220> FEATURE:
<223> OTHER INFORMATION: Nucleotide sequence of a first-red random
      adaptor part 1; n=a, c, g, or t
<220> FEATURE:
<221> NAME/KEY: random base
<222> LOCATION: (28)..(29)
<220> FEATURE:
<221> NAME/KEY: misc_feature
<222> LOCATION: (28)..(29)
<223> OTHER INFORMATION: n is a, c, g, or t

<400> SEQUENCE: 30
ctacgatacg atagggccta agagtagnn                                    29

<210> SEQ ID NO 31
<211> LENGTH: 27
<212> TYPE: DNA
<213> ORGANISM: Artificial sequence
<220> FEATURE:
<223> OTHER INFORMATION: Nucleotide sequence of a first-red random
      adaptor part 2

<400> SEQUENCE: 31
ctactcttag gccctatcgt atcgtag                                      27
```

SYSTEM AND METHODS TO QUANTIFY AND AMPLIFY BOTH SIGNALING AND PROBES FOR CDNA CHIPS AND GENE EXPRESSION MICROARRAYS

CROSS-REFERENCE TO RELATED APPLICATIONS

This application is a continuation of pending U.S. patent application Ser. No. 12/334,036, entitled "SYSTEMS AND METHODS TO QUANTIFY AND AMPLIFY BOTH SIGNALING AND PROBES FOR CDNA CHIPS AND GENE EXPRESSION MICROARRAYS" filed Dec. 12, 2008, which claims priority from U.S. patent application Ser. No. 10/380,596, entitled "SYSTEMS AND METHODS TO QUANTIFY AND AMPLIFY BOTH SIGNALING AND PROBES FOR CDNA CHIPS AND GENE EXPRESSION MICROARRAYS" filed Mar. 17, 2003, now issued as U.S. Pat. No. 7,482,443, which claims priority from International Patent Application Serial No. PCT/US01/07508, entitled "SYSTEMS AND METHODS TO QUANTIFY AND AMPLIFY BOTH SIGNALING AND PROBES FOR CDNA CHIPS AND GENE EXPRESSION MICROARRAYS" and filed Mar. 9, 2001, which claims priority from U.S. Patent Application Ser. No. 60/187,982 entitled "SYSTEMS AND METHODS TO QUANTIFY AND AMPLIFY BOTH SIGNALING AND PROBES FOR CDNA CHIPS AND GENE EXPRESSION MICROARRAYS" filed on Mar. 9, 2000, the entireties of which are hereby incorporated by reference.

BACKGROUND OF INVENTION

1. Field of Invention

The present invention relates generally to the field of detecting genes and gene expression from biological and medical samples and more particularly it relates to improving both sensitivity and quantification in comparative multi-analyte detection formats such as cDNA chips and expression microarrays.

2. Description of Related Art

Genetic analysis of an organism or tissue involves two major fields of study, the determination of existing genes and mutations as reflected in genomic DNA sequences and the evaluation of functional gene activity as reflected in the expression of messenger RNA (mRNA) transcripts or resulting protein byproducts. Since there are no reasonable means to separately detect all or most protein products simultaneously, global comparisons of gene expression have generally focused on mRNA analysis because such transcripts can be isolated and detected more simply—either by virtue of their specific sequences and or by virtue of the common presence of a poly-A tail on their 3' end. These poly-A tails allow the entire pool of mRNAs to be simultaneously copied with a single poly-T primer and the enzyme reverse transcriptase (RT) to make a single antisense strand of cDNA from each mRNA transcript in a sample. Consequently, most methods for gene expression analysis have primarily been based on assessing the relative number of RNA transcripts being produced by different genes and on comparing the timing of such gene activity. The most important goal of these methods is therefore to determine the comparative frequency of each transcript in different cells and tissues, as well as detecting any expression changes that occur in response to various stimuli, physiological conditions and pathologic states. Furthermore, such quantitative methods should have broad utility for genetics research in general and for a variety of biomedical applications including tissue typing and forensic analysis, the diagnosis and prognosis of various pathologies, conditions, and responses to therapy, and the identification of new or refined targets for pharmaceutical therapy or gene therapy.

Current art has provided few methods to globally explore gene expression differences between cells and tissues and most studies have employed differential display or cDNA subtraction analysis which provide partial non-quantitative information [Hedrick et al., Nature 308: 149 (1984); Liang et. al., Science 257: 967, (1992)]. Similarly, expression analysis by Northern blotting, RNase protection assays, or reverse transcriptase polymerase chain reaction (RT-PCR) are generally only useful for evaluating a very limited number of genes per analysis [Alwine, et al., Proc. Natl. Acad. Sci., 74: 5350, (1977); Zinn, et al., Cell, 34: 865 (1983); Veres, et al., Science, 237: 415 (1987)]. Several methods have been devised to extract cDNA copies of the 3' ends of mRNA transcripts and then characterize those fragments by restriction digests [Ivanova et. al., Nucleic Acids Res. 23: 2954 (1995); Prashar et. al., Proc. Natl. Acad. Sci., 93: 659 (1996); Kato, Nucleic Acids Res. 23: 3685 (1995); Kato, U.S. Pat. No. 5,707,807 (1998); Weissman et al., U.S. Pat. No. 5,712,126 (1998)]. While these methods expand the number of expression products that can be studied, they also remain limited in scope. Taking a different approach, Kinzler, et al. [U.S. Pat. No. 5,695,937 (1998)] have devised a more comprehensive method for measuring messenger RNA (mRNA) transcripts quantitatively by extracting and slicing out a tiny segment of the cDNAs copied from the 3' end of each mRNA transcript and then creating composite concatemers of those segments from different transcripts. The representative 9 or 10 base segments are then counted by sequencing analysis to determine the frequency of the original transcripts. However, this method involves considerable complexity and the sequencing steps are very time consuming and expensive.

The development of cDNA based gene expression microarrays provides a ready means to simultaneously assess the relative expression of hundreds or thousands of different genes from tissue or cellular samples. [Schena et al., Science, 270: 467-470 (1995); Schena, et al., Proc. Natl. Acad. Sci., 93:10614-9 (1996); Shalon et al., Genome Res., 6: 639-45 (1996); DeRisi et al., Nature Genetics, 14: 457-60, (1996); Heller et al., Proc. Natl. Acad. Sci., 94: 2150-5, (1997); Khan et al., Cancer Res., 58: 5009-13 (1998); Khan et al., Electrophoresis, 20: 223-9 (1999)] These analyses are accomplished by first preparing miniature grids or arrays on membranes or coated glass substrates wherein small but dense cDNA samples of individual genes are robotically spotted in a two dimensional pattern. Then, a total RNA or mRNA sample is copied and labeled using reverse transcriptase and a poly-T primer to create a pool of cDNA probes that reflect the mRNA expression transcripts. These labeled probes are then hybridized to their respective gene spots in the microarray in order to detect and determine the relative frequency of each transcript in the original sample. These gene expression arrays, which are commonly called expression microarrays, DNA chips, cDNA chips, or biochips, were first manufactured from gene specific synthetic oligonucleotides that likewise are created or distributed on the array in a two dimensional pattern and that can capture and detect labeled expression products in a somewhat similar manner if they are fragmented into smaller pieces [Fodor et al., U.S. Pat. No. 5,445,934 (1995); Fodor et al., U.S. Pat. No. 5,800,992 (1998)]. These commercial oligo-based DNA chips are called GENECHIPS. It should be noted that microarrays generally refer to miniature arrays on coated glass substrates, however, larger scale arrays on membrane formats employ similar chemistries and target configurations and thus are suitable for and similarly improved by the application of the present invention.

While the development of expression microarrays allows a greatly expanded overview and assessment of the relative frequency of different gene transcripts in a sample, current methods are limited by significant deficiencies in both quantification and sensitivity [Duggan et al., Nature Genetics, 21: 10-14 (1999); DiRisi et al., Nature Genetics, 14: 457-460 (1996); Rajeevan et al., Jour. Histochem. Cytochem., 47: 337-42 (1999)]. Firstly, quantification is falsely biased since labeling is proportional to probe length, and thus, short genes give less signaling per probe than long genes. Secondly, even long genes provide limited signaling with cDNA chips when compared to the signaling provided by the far longer segments that are typically used for mapping genes to chromosomes or nuclei. In addition, labeling is also limited for expression microarrays because fluorescent compounds, such as Cy3 and Cy5, which are commonly employed for comparative two color labeling, are poorly incorporated by reverse transcriptase. Moreover, current methods are especially limited in sensitivity when individual genes of interest have been down-regulated or are weakly expressed or when the total sample available for study is quite small. In either case, specific or multiple gene transcripts of interest may produce an insufficient number of labeled probes to be detected. Thus, current cDNA chip methods are generally poor or inadequate for detecting specific mRNA transcripts that are expressed in frequencies of less than 10 copies per cell or for analyzing samples comprised of: a) less than 0.5 milligrams of tissue, b) less than 50 micrograms of total RNA, b) less than 0.5 micrograms of poly-A mRNA, or c) less than 5 million cells [Duggan et al., Nature Genetics, 21: 10-14 (1999)]. The conjunction of these deficiencies in both quantification and sensitivity additionally creates further problems. Thus, short genes may falsely appear inactive or weakly expressed relative to longer genes in the same sample, and longer genes will falsely appear to be expressed more abundantly relative to shorter genes. Consequently, more accurate and sensitive detection methods are needed.

One approach to improve chip detection would be to amplify mRNA derived probes by the polymerase chain reaction (PCR) or related enzymatic methods. However, commonly available PCR procedures such as RT-PCR and multiplex PCR, have only been used successfully to amplify a limited number of the gene products in a sample since effective multi-analyte amplification typically requires the provision of at least one unique primer for each type of gene product amplified [Sutcliffe et al., U.S. Pat. No. 5,807,680 (1998)]. In related art such as differential display or other older procedures to explore expression differences, global amplification methods have been employed based upon using simple arbitrary primers, hexamers or various random primer constructs instead of unique primers to amplify DNA or RNA. The inconsistency of such methods, however, have only made them useful for identifying unusual or novel gene expression products, and they have not been devised or employed for use with expression microarrays or DNA chip analyses [Welsh et al., to Nucleic Acids Res., 18: 7213-18 (1990); Pardee et. al., U.S. Pat. No. 5,262,311 (1993) and U.S. Pat. No. 5,665,547 (1997); Liang et al., Nucleic Acids Res., 21: 3269 (1993); Mou et al., Biochem. Biophys. Res. Comm., 199: 564-569 (1994); Villeponteau et al., U.S. Pat. No. 5,580, 726, (1996); Silver et. al., U.S. Pat. No. 5,104,792 (1992); Tavtigian et al., U.S. Pat. No. 5,789,206 (1998); Shuber, U.S. Pat. No. 5,882,856 (1999)]. The prime difficulty with many of these methods derives from the use of short arbitrary or random primers that can give variable results with different temperature and hybridization conditions such that they are unsuitable for diagnostic analyses. Even RT-PCR or multiplex PCR methods, which employ unique primers, can produce semi-quantitative rather than quantitative results since different primer sets vary considerably in efficiency and since kinetic factors favor copying the smaller and more abundant products with those methods. Therefore, some products may not amplify well, and rare or down-regulated transcripts may be under-represented [Khan et al., Electrophoresis, 20: 223-9 (1999)]. Additionally, mammalian mRNA samples include very large gene transcripts 6 to 12 thousand nucleotides long that cannot be amplified reliably by routine PCR methods. Consequently, global PCR amplification of a pool of mRNA-derived cDNA probes has not been attempted or successfully accomplished for DNA chip or expression microarray analyses, and based on the above reasons, it has been scientific dogma that exponential amplification methods cannot be validly applied to multi-analyte gene expression arrays. Nonetheless, less robust linear amplification has been developed and employed for chip analyses by adding a RNA polymerase promoter to the end of the poly-T primer used for RT. However, such amplification is incremental and finite, with a typical duplication of 20-60 copies, and the amplified products it produces are antisense RNAs which are degradable [Phillips et. al., Methods, 10: 283-288 (1996); Kondo et al., U.S. Pat. No. 5,972,607; VanGelder et al., U.S. Pat. No. 5,716,785 (1998)]. In related art, Wang et al., [U.S. Pat. No. 5,932,451 (1999)] refined such methods to allow asymmetrical PCR amplification of ds cDNA made from an mRNA sample. However, this amplification method is similarly limited in the number of copies that can reasonably be made from the original sample (68 fold duplication demonstrated). More importantly, by copying full length probes, the signaling bias of current methods cannot be overcome since the number of labels incorporated per probe is a large variable dictated by the transcript size of different genes, and in common mammalian species including humans, transcripts vary from several hundred bases to twelve thousand bases or more. These problems therefore suggested that improved detection might be better achieved by amplifying signaling rather than the target sample.

As described in PCT/US99/16242 (WIPO Publication WO 00-04192), corresponding to U.S. patent application Ser. No. 09/744,097 filed Jan. 16, 2001 entitled "Methods for Detecting and Mapping Genes, Mutations and Variant Polynucleotide Sequences," which is hereby incorporated by reference herein for all purposes, methods and compositions for modular probe and reporter systems that improve the specific detection of genes and mutations and that amplify signaling were disclosed. These disclosed compositions and methods include:

1. Probe methods, known as WRAP-PROBEs, that are manufactured from synthetic DNAs, from PCR (polymerase chain reaction) products, or from cloning products, wherein the probes have a central, target-specific sequence that is helically wrapped around the target strand, and wherein they have one or more generic linkers at one or both ends that bind one or more reporters. By binding separate reporters to the ends of the probes after coiling the probes around the target, the reporters are more effectively tethered, and they thereby provide far more effective signaling than is achieved with simple labeled probes. Indeed, this method can provide multifold signal amplification if dual chains or arrays of long labeled reporters are bound to a short WRAP-PROBE of this configuration. This WRAP-PROBE composition also provides an economic advantage in being able to use generic linkers to interchangeably bind either different reporters to the same probe or different probes to the same reporter, wherein a series of generic reporters may be applied that vary in both the type of signaling and in signaling intensity.

2. Generic reporter methods and compositions such as GENE-TAGs and TINKER-TAGs, these reporters include liner segments of double stranded DNA or chained and joined polynucleotides with single stranded linkers at one or both ends that can join together in arrays and can join to the linkers of WRAP-PROBEs or related probes to provide amplified signaling.

3. DNA-based connectors called Multi-LINKERs, including singular or composite polynucleotide structures that join to the linker of a probe and provide two or more secondary linkers in order to bind multiple reporters to a probe.

The related WRAP-PROBE methods and compositions are suitable for making targeted probes that amplify signaling and that more efficiently map or detect a specific gene sequence in a variety of detection formats such as in situ gene mapping, dot blots, etc. In those formats, the target or targets are on the substrate and a small number of labeled probes are individually manufactured in excess quantity to find and label those specific targets. The object is simply to put label on the target, thereby mapping or counting the targets. However, those methods are not suited for DNA chip or microarray gene expression formats where the chip substrate is in fact a set of capture probes and where the probes applied to the chip are the true targets of the assay. Thus the object of an expression assay is to determine the relative frequency of the mRNA transcripts in the original tissue sample, and the array is just a device to capture and count a labeled probe set derived from the sample. Thus this probe set must maintain its relative frequencies—accurately representing the thousands of different gene transcripts in the original tissue. Consequently, WRAP-PROBEs for expression array analysis cannot be individually manufactured in the same way as prior WRAP-PROBEs were separately tailored to specific genes.

SUMMARY OF THE INVENTION

The present invention provides methods and compositions of matter that allow quantitative, sensitive and rapid analysis of gene expression patterns in different cells and tissues as a means to detect functional changes associated with development and physiology, to diagnose abnormal variations related to disease, and to discover and assess pharmaceutical agents. The invention is designed for and particularly suited to multiple analyte formats such as cDNA chips and expression microarrays where the diagnostic value would be improved by increased signaling and by determining the true frequency of different mRNA transcripts in a sample and not just their approximate frequency—a standard poorly addressed by current methods. The invention is complementary to prior inventions of the applicant which provide a probe construction, known as WRAP probes, for detecting genes and nucleotide sequences, which employ generic reporters such as GeneTAGs or TinkerTAGs that are linked to terminal linkers of the probes, and which may employ multi-linker components to join multiple reporters to each probe.

The present invention employs novel primer, linker, adapter, extender and reporter compositions and molecular processing methods to globally transform a mixed pool of mRNAs into a pool of modified cDNA-based probes, called WRAP-Probes, that have common universal linkers at one or both ends for joining reporters, to thereby provide more defined signaling as well as greater signaling potential. The basic principle of these methods is to achieve signaling by affixing generic reporters to the ends of the probe, either directly or via terminal linkers, rather than by labeling the target specific segment which varies in size for each gene. This invention thus allows quantitative analysis of expression since the signaling element is effectively equalized for each transcript detected, and it improves sensitivity since reporters can be affixed that have greater signaling potential than a labeled probe. Alternate embodiments of the probes, the multi-linking units, and the generic reporters have been devised and these components can be used together in a modular manner to achieve different detection and signaling objectives.

When the set of WRAP-Probes is constructed with common universal linkers on both ends, this configuration creates an opportunity to use these linker sequences as global primers, thereby allowing the duplication of the entire pool of probes by exponential amplification procedures such as PCR. Alternate amplification methods were invented that produce either singular WRAP-Probes from each mRNA transcript or a fragment series of smaller WRAP-Probes from each transcript. These methods include novel compositions and procedures to create truncated probes and to affix double-linker/primer sites so that they can be reliably amplified by exponential methods. The probes are then globally amplified and labeled during PCR with a single primer set. These amplified probes can also achieve signaling quite simply and inexpensively with new compositions called ChipTAGs that are composed of one or more labeled polynucleotides which additionally serve both linker and primer functions. Thus effective methods were devised that transform a mRNA pool into a set of smaller probe subunits which are globally amplified and suitable for the analysis of gene expression with cDNA chips or microarrays. These methods and compositions improve the quantification of gene expression and allow highly improved detection of rare transcripts and or very small samples.

To overcome the difficulties of current compositions and methods and to still obtain the signaling advantages of the WRAP-PROBE invention, in the present invention, reagents and probe systems that extend the WRAP-PROBE design to expression array applications by globally converting a complex pool of mRNA transcripts into a pool of probes having common universal linkers on one or both ends have been developed. However, the present invention differs compositionally from the prior invention because the functional product of this invention is not a solitary WRAP-PROBE, but in fact a composite set of WRAP-PROBEs that necessarily contains multiple probes of considerable diversity with important differences in relative frequency. While it would be possible to make individual WRAP-PROBEs from single genes in a pool of mRNA products in the same manner as RT-PCR is applied to individually copy and amplify a single mRNA gene product and determine its presence, such an approach would be costly, inefficient and would introduce bias. (This approach would require the manufacture of gene specific primers for each gene target wherein the primers would additionally have a universal linker on their 5' end.) Therefore, the present invention devises and discovers a composite probe set of WRAP-PROBEs wherein the probe set shares common universal linkers that enable the joining of common reporters and that enable the global exponential amplification of the probe set. Because of the high number of diverse probes involved, it is important that the universal linkers applied to the probes do not bind non-specifically to target sequences on the chip. The present invention adds an important second function, exponential amplification, to the universal linkers of the WRAP-PROBE configuration, and it additionally provides methods to globally create and amplify the probe set as a collection of probes. To distinguish this probe set composition, these new probes were intentionally called REX-WRAP probes in the applicant's U.S. Provisional Patent Application Ser. No. 60/187,982, filed Mar. 9, 2000, entitled "Methods to Quantify and Amplify Both Signaling and Probes for DNA Chips and Gene Expression Microarrays", which is hereby incorporate by reference herein for all purposes, to indicate their different source, form and function as a collection or set of RNA-derived gene expression probes. However, for linguistic fluidity in this present description, this probe set devised for expression arrays will simply be termed WRAP-Probes.

A basic principle of the present WRAP-Probes invention is to achieve more sensitive and quantitative results with expression arrays by adding equivalent reporter signaling to the terminal linkers of the probe set. This approach contrasts with the current practice of labeling the probes internally—a method causing length-related bias in signaling. This end labeling approach equalizes signaling per probe and provides a truer count of transcript frequency, and it also allows far greater signaling per probe by adding multiple reporters. Additionally, the dynamic range of linear signaling is improved since the standard method can saturate signaling early for those genes that are both long and abundant. Moreover, other advantages can accrue from not labeling the target specific segment with bulky signaling molecules that are poorly incorporated, such as Cy3 and Cy5. And finally, it is known that the target strands of cDNA spotted arrays lie side by side in tight clusters making probe hybridization more difficult with large signaling molecules attached to the bases [Duggan et al., Nature Genetics, 21: 10-14 (1999]. Notwithstanding these considerations, labeling can still be applied to the probes directly to provide additional signaling.

Applicant has devised alternate embodiments of the WRAP-probes method as well as alternate embodiments wherein probe sets are combined with different reporters or intermediate linkers. To this end, applicant has devised and discovered different universal linkers that provide probe sets that will bind different reporters, thereby enabling comparative analysis of different probe sets from different samples on the same expression array.

The most elemental version of the WRAP-Probes method is to create probes with a single universal linker on one end to enable the binding of a generic reporter, such as a GeneTAG or TinkerTAG reporter (previously described as GENE-TAGs and TINKER-TAGs in more detail in International Patent Application Serial No. PCT/US99/16242). Applicant has devised and discovered a preferred embodiment of this method by copying the mRNA from the 3' poly-A end by reverse transcriptase (RT) using a modified poly-T primer with universal linker sequences added to the 5' end. The terminal linker thus created provides a binding site to attach reporters either before or after the probe is hybridized to the expression array. The resulting probes are called One-Linker WRAP-Probes. A variety of such modified poly-T primers are devised to allow a multiplicity of reporter attachments.

Applicant has devised alternate methods that produce a probe set with two linkers, known as Double-Linker WRAP-Probes. These methods similarly create single-stranded or double-stranded cDNA probe components with a modified poly-T primer having a 5' universal linker, and then a second linker is added to the opposite end so that reporters can bind to two linkers—pulling on the helically bound probe from both ends as with a prior WRAP-PROBE. This double-linker configuration provides a structural advantage for tethering longer or multiple reporters, and it additionally enables the amplification of the probe set. Applicant has devised and discovered several methods and compositions for creating such Double-Linker WRAP-Probes based on joining novel adapter compositions to the 3' end or based on applying novel extender compositions to extend the 3' end and form a second universal linker.

Several types of adapters and extenders have been devised and discovered. Adapters consist of paired polynucleotides joined together but with a single stranded overhang, wherein the overhang provides a binding site to join the adapter to a DNA segment with a complementary cohesive end, and wherein the paired segment provides appended sequences that serve a recognition, joining or primer function. The adapters of the present invention have universal linker sequences in the paired segment, and they differ in the overhang. One type of adapter of the present invention, called a Specific Adapter, has a small overhang specific to a restriction cut site. Another type, called a Random Adapter, has an overhang of a few random bases. A third type, called a Homopolymeric Adapter, has an overhang of poly-C or poly-G sequences. These adapters are designed to join and ligate onto the 3' end of a cut or modified probe segment to form a second universal linker. The extenders of the present invention consist of a polynucleotide with universal linker sequences on their 5' end and a 3' end with either random or homopolymeric sequences. The homopolymeric extender of the present invention has 3' poly-C or poly-G sequences and is joined to a 3' probe end of complementary poly-G or poly-C sequences formed with terminal transferase, whereupon the 3' end of the probe may be further extended with the universal linker sequences using the extender product as a template. Alternatively, the present invention provides a novel extender with a random 3' end that is used in a similar manner except that it can join anywhere along the probe. It only functions as an extender in the present invention when it joins to the 3' end of the probe via the random sequences, whereupon the universal linker sequence provides a template for polymerizing a 3' extension of the probe to provide a second linker end. In the present invention this special extender, called a Random End-Linker, is employed with a novel procedure of the invention, called Back-Tagging, whereupon repeated thermal cycling steps similar to PCR are employed to make many attempts at putting the Random End-Linker at the far 3' end of the probe to extend it, wherein the Random End-Linker is preferentially modified at the 3' end to block forward polymerization on the probe template. Consequently, the Random End-Linker preferentially back-extends the 3' end of the probe to form a second universal linker and it avoids making partial copies of the probe itself by forward polymerization.

The above adapter and extender compositions and related procedures of the present invention enable the simultaneous global application of a second universal linker to the 3' ends of the probe set to form Double-Linker WRAP-Probes. While such Double-Linker probes can bind at least twice as many reporters as One-Linker probes, either version gives equivalent signaling per transcript within a sample, and thus true counting of gene expression frequencies. Where true transcript counting may be sacrificed for greater sensitivity, applicant has also devised secondary embodiments of the Double-Linker WRAP-Probe methods described above, wherein multiple short probes are created from each mRNA transcript, either by fragmenting the RT products or cutting them with restriction enzymes, and by employing various adapters or extenders to construct a series of short WRAP-Probes from them. Applicant has also devised alternate embodiments of these probe variants wherein the linkers are pre-attached to labeling agents, multi-linkers, or reporter constructs.

Applicant has also devised variations of these fragmented probe procedures to apply to the original WRAP-PROBEs method for detecting single genes or sequences in several in situ hybridization formats such as RNA arrays, single tissue preps or tissue arrays, [Kononen et al., Nature Medicine 4: 844-47 (1998)] as well as for the mapping of particular gene sequences in genomic DNAs, nuclei and chromosomes; e.g. FISH mapping (fluorescent in situ hybridization). In such cases, cloned or PCR copies of specific genomic DNA or mRNA targets are transformed into a subset of mini-WRAP-Probes with linkers at one or both ends. Applicant has devised several embodiments by cutting the full length probe components into smaller segments with restriction enzymes, shearing, RNase enzymes and the like and then universal GeneTAG linkers are applied to one or both ends by modifications of the above mentioned procedures for putting the second universal linker on the 3' end of Double-linker WRAP-Probes. The hybridization of these fragment probes to target tissues provides multiple adjacent probes along a target, and thus highly amplified signaling since each probe can bind one or more generic reporters (e.g. GeneTAGs) with greater signaling capacity than a simple labeled probe.

Applicant has also devised WRAP-Probes that are created with multiple linkers and or multiple reporters pre-attached to one or both ends. These configurations are achieved by attaching generic reporters such as GeneTAGs or TinkerTAGs to a Multi-Linker or by attaching smaller signaling elements directly to the distal linkers of a Multi-Linker unit.

Applicant has devised and discovered signaling compositions, called ChipTAGs, which are short polynucleotides conjugated to one or more labeling agents, that serve as a reporter joined to a universal linker and that additionally serve a primer function. Similar short reporter compositions called OligoTAGs, that only served a linker and labeling function, were previously described in International Patent Application Serial No. PCT/US99/16242 as end-labeled oligonucleotides that were secondarily joined to a Multi-LINKER unit. The advantages of using these ChipTAG components as linkers, primers and reporters are improved cost and efficiency. When bulky fluorescent compounds such as Cy3 or Cy5 are joined to nucleotide reagents for enzymatic incorporation, they are extremely expensive and they are poorly incorporated into probe or reporter units (1-2% efficiency). In contrast, the same or similar labeling agents can be chemically conjugated to an oligonucleotide or polynucleotide more reliably (98-99% efficient) and both reagent cost and manufacturing are relatively inexpensive.

Applicant has also devised two or more sets of GeneTAG, TinkerTAG, ChipTAG and Multi-Linkers, with different linkers and different labeling, so that two or more samples can be labeled differently and simultaneously compared on an array to determine relative differences in expression levels between samples.

Applicant has also devised modified poly-T primers to generate WRAP-Probes that are pre-attached to one or more direct or indirect signaling elements, that are pre-attached to Multi-LINKERs, with or without signaling elements attached, and/or that are pre-attached to labeled GeneTAGs, TinkerTAGs or other generic reporters. The most elemental of these dual function compositions are a modified poly-T primer with a label agent such as Cy3 or Cy5 conjugated to the 5' end of the primer, with a preferred embodiment having a universal linker sequence on the 5' labeled end to add further reporters. The advantage of these methods is that by joining probes and reporters beforehand, one or more hybridization step can be eliminated.

Applicant has also devised WRAP-Probes that employ either modified poly-T primers, Multi-LINKERs, GeneTAGs, TinkerTAGs or ChipTAGs, that are not based on fluorescent or radioactive labeling, but rather, they are labeled with refractory or light scattering particles or with metallic or semiconductor based signaling elements—alternatively allowing the detection of microarrays or DNA chips with novel optical or photonic sensors or with micro-electronic circuits or sensors.

The above-described Double-Linker WRAP-Probe methods also allow a major methodological departure from the general principle of creating labeled cDNA probes from each mRNA transcript. Namely, when a universal linker sequence is created on both ends of each probe, those sequences can be designed and used as generic primer sites for globally copying and amplifying the entire pool of probes with a single primer set or even with a single primer using common PCR methods or related processes. Applicant has devised and discovered methods to make such globally amplified WRAP-Probe probe sets. These methods employ in part one of the above described double-linker compositions and procedures (based on the ligation of adapters or the annealing of extender templates) to apply a second linker to the first strand cDNA copy which already has a first linker created by the modified RT primer. However, these copying methods are modified for global amplification since exponential PCR of full length copies, particularly of the longer transcripts, may produce bias and deficiencies in the amplification products as described above. Therefore, two preferred WRAP-Probe amplification procedures have been devised; 1) to make a single WRAP-Probe from a shortened 3' end of each transcript, or 2) to cut and transform full length or near full length cDNA copies into a set of multiple short probes called Mini-WRAP-Probes. Either of these procedures produce a pool of short probes all having generic linker/primer sequences at each end so that they are suitable for exponential amplification.

Therefore, the basic principle of the amplified WRAP-Probe method is to construct or reconstruct RT generated cDNA probes as short or shortened probes of similar length, with generic linkers on both ends that provide universal primer binding sites independent of gene specific sequences, so that the entire set of mRNA derived probes can be globally amplified by PCR in a unbiased manner. This invention provides several important advantages. First, expression analyses can be conducted on very small RNA or tissue samples. Second, quantitative signaling can be preserved either by attaching generic reporters to the ends of the amplified probes or by shortening the probes to approximately the same length so that internal labeling becomes more equalized between genes. Third, since all products are amplified with a single primer set, all templates have essentially equalized access to primers, and thus any bias towards amplification of the more abundant transcripts is reduced or eliminated. Fourth, by amplifying the probes, more limited or economic signaling methods can be employed such as ChipTAGs since the number of labeled probes can be exponentially increased. And finally, the amplified probe set effectively increases the concentration of the sample thus allowing larger chip formats—that is the same tissue or RNA sample can produce sufficient probes to cover a larger chip hybridization area enabling simpler, less miniaturized, and less expensive chip manufacturing processes.

Applicant has devised and discovered three primary new methods to globally achieve short double-linker probes from mRNA that are suitable for PCR amplification: 1) restriction cutting and adapter ligation, 2) globally truncated RT and probe extension with a random end-linker, and 3) globally truncated RT and random adapter binding. These methods are based upon and modified from the Double-Linker WRAP-Probe methods described above.

For the first sub-method, applicant has devised and discovered procedures to achieve short probes by cutting the initial cDNA products with one or more restriction enzymes; capturing the cut fragments from the poly-A end; and ligating a matching adapter to the opposite end to provide the second linker/primer sequence needed for PCR amplification. Since the cut sites vary for different genes, enzyme selection is significant, and thus it is preferred that two enzymes are employed in separate samples to ensure that no gene lacks representation in the probes.

For the other sub-methods, applicant has devised and discovered procedures to globally achieve short probes of similar length by dramatically truncating the RT protocol, from the typical exposure time of one or two hours, down to brief exposures of a few minutes or less. Standard RT protocols, including manufacture of probes for DNA chips, are typically based on one or two hour RT exposures to ensure that the full length of all transcripts is copied since prior work had established that 95% of RT copying is completed in about 50 minutes [Verma et al., Nature New Biology, 235: 163-169 (1972); Verma et al., Biochem. Biophys. Acta, 473: 1-38 (1977); Gubler et al., Gene, 25: 263 (1983)]. However, by radically cutting the RT enzyme extension time down to a period of minutes or seconds, applicant has discovered that the RT products are truncated prematurely in relatively equivalent lengths—producing a pool of cDNA probes that are randomly and arbitrarily short—regardless of the gene length of the original mRNA transcripts. This novel protocol, called Short-RT, in effect equalizes the length of all probes to a narrow size range dictated somewhat randomly by when each transcript starts the copying process relative to the instant that RT enzyme exposure begins. The resulting pool of randomly short products, that are mostly hundreds of bases long vs. thousands of bases long, are easily amplified by PCR. More importantly, the known bias that occurs in amplifying different gene products of different length is effectively overcome by this random length sampling method. This key modification, Short-RT, provides a simple, economic method to remove an important barrier to unbiased exponential amplification, gene length variation, which has inhibited the prior development and use of PCR-based protocols for DNA chip applications as well as other global mRNA comparisons.

Therefore, for the second sub-method, globally truncated, Short-RT products are prepared with a first universal linker, and then the extender reagents described above as Random End-Linkers are applied to create a second universal linker. While these extenders can bind anywhere along a probe, a significant result only occurs when they bind at the 3' end, wherein that 3' probe end is back extended with a linker sequence that forms a primer binding site. Therefore, the protocol called Back-Tagging described above was devised and discovered to increase the opportunity for such an end extension to occur. This novel protocol commonly employs rapid thermal cycling for approximately 100 to 200 cycles that mimic the steps of PCR (1. denaturing at high temperature, 2. annealing at low temperature, and 3. briefly extending at moderate temperature) but do not practice PCR since the 3' end of the Random End-Linker is typically blocked. Whereupon, the extenders are repeatedly hybridized to the probe to extend it with a universal linker, thereby providing the second linker/primer site needed for subsequent PCR amplification of the probes. Moreover, since the probes are of randomly truncated length, they can also be internally labeled, during or subsequent to PCR amplification, instead of or in addition to end labeled, without reintroducing signaling bias between different genes.

For the third sub-method, globally truncated, Short-RT products are again prepared with a first universal linker, and the second linker is then applied to the 3' end of the probes with the novel Random Adapter described above which has a short random overhang. The random segment provides a random binding mechanism to anchor the adapter on the 3' end of any probe so that probe and adapter components can be ligated together. After ligation, the adapter-probe complex is denatured and purified to release the unbound half of the adapter—thus providing probes containing linker/primer sites on both ends suitable for PCR amplification. For the same reasons as above, this sub-method also allows the probes to be internally labeled, instead of or in addition to end labeled, without reintroducing signaling bias between different genes.

Elements of the above sub-methods can also be combined together in different ways or combined with pre-existing technologies to alternatively produce double-linker probes from single or double stranded cDNA probes made with a 5' first linker. For example, globally truncated, Short-RT products can be prepared with a modified RT primer, converted to double stranded cDNA probes, and joined to commercial adapter/linker products, e.g. Clontech's Smart or Marathon adapter products, to create a 3' second linker site on the probes. Alternatively, globally truncated Short-RT products can be prepared with a first universal linker using the Modified Poly-T primer, and then, a homopolymeric 3' tail of poly-C or poly-G sequences is provided [Ivanova et. al., Nucleic Acids Res. 23: 2954 (1995)]. Thereafter, an extender polynucleotide with a 3' matching homopolymeric segment is applied to create a second universal linker. Alternatively, an adapter could be made with a 5' universal linker and a homopolymeric 3' end that would allow this product to be ligated to the 3' end of the probe creating a second universal linker. These alternate procedures provide additional methods to affix the second linker/primer sequence required for global PCR amplification of the probe set.

Finally, the applicant has devised adapters and extenders applicable to the above methods that provide second linkers on the 3' end that mirror the first linker sequences of the 5' end whereupon the probes can be linked similarly via each end as well as amplified by PCR with a single primer rather than a pair of primers.

With these new methods, the primers used for global amplification of the WRAP-Probe probe set or the Mini WRAP-Probe probe set can employ simple ChipTAG compositions to generate probes with pre-attached terminal labels. Due to exponential amplification of the probes, such limited signaling can be quite sufficient. Alternatively, the primers can be pre-attached to multi-linkers or reporters such as GeneTAGs that provide greater signaling per probe. Either approach will allow a single hybridization step to apply both probes and reporters.

Current art has not been able to employ exponential amplification methods for expression arrays because of one or more of the following: 1) the need for multiple unique primers, 2) the variability's and deficiencies of employing hexamers or random primers as a substitute for unique primers, and 3) the great variation in gene transcript size which can alter amplification characteristics. The amplified WRAP-Probes and Mini-WRAP-Probes devised and discovered here set a new precedent in signaling potential for expression arrays. By creating one or multiple short probes from each transcript and by using one universal primer set for the entire pool of probes, the bias of global amplification is avoided. Moreover, the creation of globally short probes provides considerable advantages for application to DNA chips or microarrays since short probes improve both the kinetics of hybridization and access to small target opportunities on the chips. The WRAP-Probe method produces one amplified probe product per transcript and thus preserves the principle of generating equivalent signaling per transcript as with non-amplified WRAP-Probes. The Mini-WRAP-Probe method relaxes that principle for the sake of simplicity and greater signaling, and yet it still does not depart further from the signaling differences per transcript that are inherent in the current art of labeling probes along their length. This Mini-WRAP-Probe method is also well suited to expression arrays based on specific oligonucleotides on the chip vs. spotted cDNA, and in that case the multiple products from each transcript does not bias signaling since each oligonucleotide segment on the chip is known and accounted for separately. In any case, these new methods provide the first global procedures to amplify mRNA derived probes for gene expression arrays in an exponential manner. Consequently, these methods are highly advantageous over current art that requires large amounts of mRNA per each microarray assay. In contrast, these exponential amplification methods allow the analysis of very minute samples that may be available from micro dissections, needle biopsies, small blood samples, forensic traces or archived tissue as well as repeated analysis of the same sample. These advantages are particularly relevant for clinical or forensic specimens where only a single, small sample may be available. Finally, these global probe amplification procedures will allow the repeated testing of gene expression changes over time due to development, disease, or induced responses to drugs or therapies.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate one embodiment of the invention and together with the description, serve to explain the principles of the invention.

FIG. 1 depicts the creation of cDNA probes with a universal linker from mRNA transcripts and applying them to provide amplified and quantified signaling. Step 1 depicts binding the modified poly-T primer with a universal linker to the poly-A tail of mRNA and polymerizing first strand cDNA probes with a universal linker; Step 2 depicts binding the probes to a cDNA chip; Step 3 depicts binding labeled GeneTAG reporters to the universal linkers of the probes.

FIG. 6A depicts the probes hybridized to the chip that are internally labeled with Cy3 (green). FIG. 6B, the lower portion, depicts the GeneTAGs hybridized to the probes of 6A above wherein the GeneTAGs are labeled with Cy5 (red) and showing increased signaling with GeneTAGs. In this document, the color array images were converted to black and white and inverted since the array images are artificial, scanned pseudocolor images not true photographic images.

FIG. 7 depicts PCR amplified probes hybridized to the chip that are internally labeled with Cy3 (green). This image is also converted to black and white and inverted from a pseudocolor green image.

FIG. 8 depicts GeneTAGs hybridized to the probes of FIG. 7. wherein two layers of GeneTAGs are applied and the GeneTAGs are labeled with Cy5 (red) showing increased signaling. This image is also converted to black and white and inverted from a pseudocolor red image.

FIG. 9 depicts a small sample of the probes from Example 2 above that were re-amplified by PCR and applied to another expression microarray. In this case a "Red" ChipTAG primer was employed as a single primer to globally amplify and label all the probe products. Thus labeling was achieved from a single Cy5 fluor that is conjugated to the 5' end of the ChipTAG primer. Additional ChipTAG primer was added back to the probe sample after PCR amplification to increase signaling. This image is also converted to black and white and inverted from the red pseudocolor image.

DETAILED DESCRIPTION OF THE INVENTION

Figure 1:
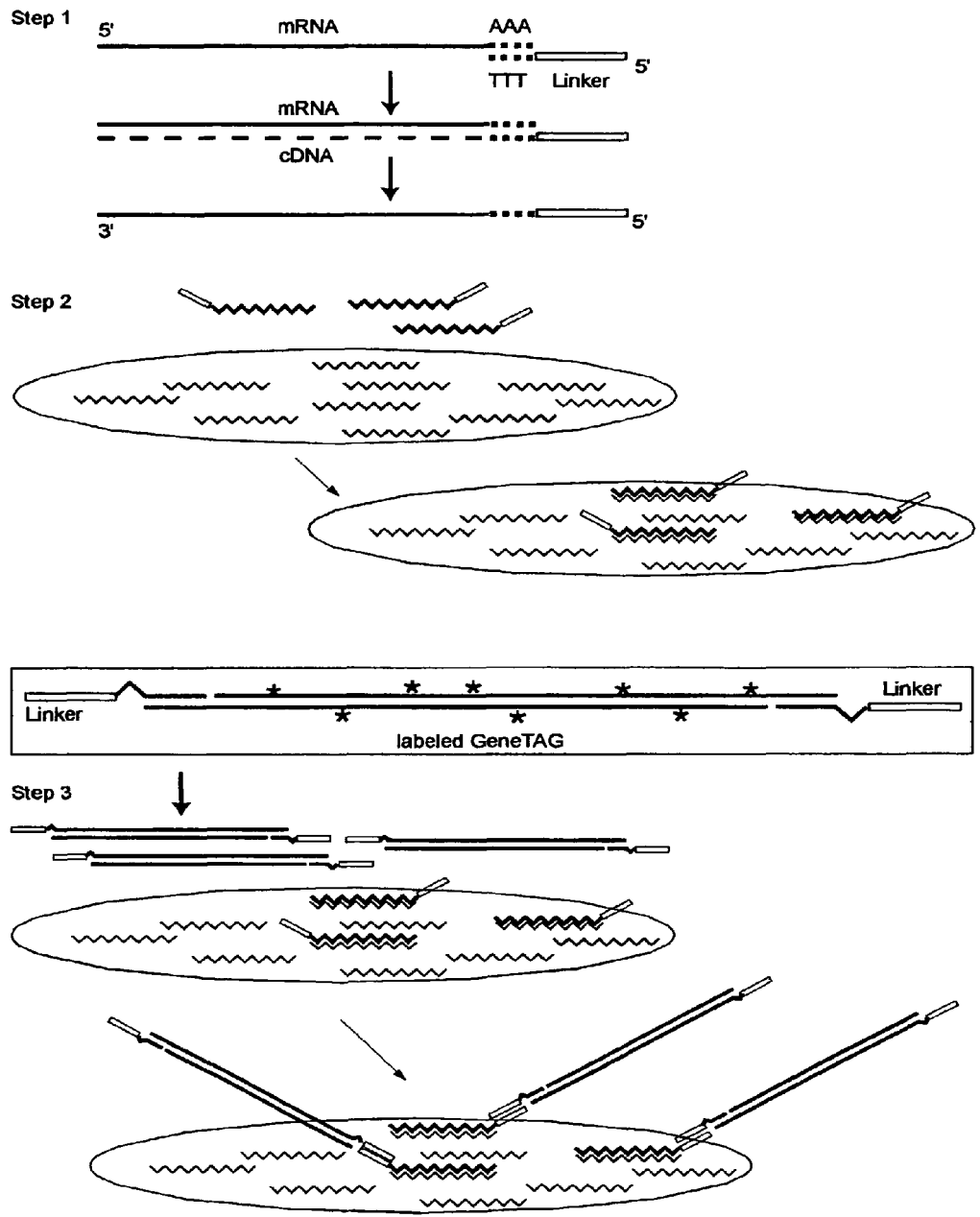
FIG. 1: One Linker WRAP-Probe method.

Preferred embodiments of the invention are now described in detail. Referring to the drawings, like numbers indicate like parts throughout the views. As used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. In the foregoing discussion, the following terms will have the same meaning as provided in International Patent Application Serial No. PCT/US99/16242 except as modified and/or expanded herein unless the context clearly dictates otherwise.

WRAP-Probe: a single DNA based probe affixed with universal linkers on one or both ends to bind generic reporters.

WRAP-Probe probe set: a pool of WRAP-Probes made from a pool of mRNA species to represent and detect relative RNA transcript frequencies with gene expression arrays.

One-Linker probes: WRAP-Probes with one universal linker.

Double-Linker probes: WRAP-Probes with universal linkers on both ends.

Amplified WRAP-Probes: a pool of WRAP-Probes exponentially amplified by PCR or related processes.

Mini-WRAP-Probes: a series of small WRAP-Probes made from fragmenting first strand cDNAs from a pool of mRNAs.

GeneTAG: linear generic reporter molecules with terminal universal linkers.

TinkerTAG: GeneTAGs constructed of partially overlapping polynucleotides that self assemble, with or without single stranded arms for binding labeled oligonucleotides.

ChipTAG: small multi-function labeled universal linker that also serves as a primer.

Universal Linker: a single stranded nucleotide sequence that allows the joining of two probe and or reporter elements by complementary nucleotides while the linker sequences are not complementary to the target sequence.

Multi-Linker: a polynucleotide or complex of polynucleotides that self assemble and that provide a probe linker and two or more reporter linkers.

Modified Poly-T Primer: a global poly-T primer for RT reactions modified on the 5' end typically with a universal linker and/or a capture moiety, label, reporter or multi-linker.

Adapter: paired polynucleotides with blunt or cohesive ends for joining to DNA fragments and providing added functions such as a linker, primer or reporter binding functions.

Specific Adapter: a composite of paired polynucleotides with an overhang of specific sequences that can be joined to restriction cut ends of DNA fragments and that provide a universal linker.

Random Adapter: paired polynucleotides with an overhang of random sequences that can be joined to any DNA fragment and that provide universal linker sequences.

Homopolymeric Adapter: paired polynucleotides with a Poly-C or Poly-G overhang that can be joined to a Poly-G or Poly-C sequence and that provide universal linker sequences.

Homopolymeric Extender: extender polynucleotide with a 5' universal linker end and a 3' Poly-C or Poly-G end that can join to a 3' Poly-G or Poly-C end of a probe and serve as a template to extend the probe with a universal linker sequence.

Random End-Linker: extender polynucleotide with a universal linker region on the 5' end and a random sequence region on the 3' end that can join to the 3' end of a DNA segment and serve as a template to extend that DNA segment with a universal linker sequence, said extender being preferably modified on the 3' end to block capacity for polymerase extension.

Probe Modifier: a category representing any of the above adapters and extenders that apply a universal linker to the 5' or 3' end of a probe, including the random adapter and extender, the homopolymeric adapter and extender and the modified poly-T primer, as well as including the ChipTAG labeled primers which add label directly onto to the end of probe when used to amplify a double linker probe.

Short-RT: modified RT protocol in which all products are stopped short during RT extension to produce similarly short cDNA probes suitable for PCR amplification.

Back-Tagging: modified thermal cycling protocol for applying Random End-Linkers to back-extend probes using multiple thermal cycling steps with short extension times.

mRNA: messenger RNA transcripts which are a subset of total RNA.

cDNA: DNA copies of mRNA

Microarray: a miniaturized grid of nucleic acid targets to detect a pool of probes.

cDNA chip: a cDNA based microarray.

Expression Array: a grid of nucleic acid targets based on cDNA or cDNA sequences PCR: polymerase chain reaction to amplify DNA exponentially.

RT: reverse transcriptase enzyme method to copy RNA.

RT-PCR: reverse transcriptase plus PCR to copy and amplify a specific mRNA transcript.

Hybridize: formation of specific hydrogen bonding interactions between complementary strands of nucleic acids.

Cross-link: covalent linkage between hybridized nucleic acid strands.

PUVA: psoralen plus UVA crosslinking procedure.

TA site: nucleotide sequence reading 5'-3': thymidine, adenine.

C9: a spacer that is 9 carbon atoms long.

C18: a spacer that is 18 carbon atoms long.

UNG: Uracil-Nucleotide-Glycosylase procedure where Uracil bases are incorporated into DNA to make them labile to glycosylase digestion.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The present invention relates to a number of probe compositions, manufacturing compositions, and signaling compositions and associated methods that improve the preparation, application and detection of probes and reporters for gene expression arrays and related multi-analyte hybridization assays, including but not limited to cDNA chips, oligonucleotide chips, biochips and other microarray formats. The present invention is in part based upon or incorporates prior inventions of the applicant, described in International Patent Application Serial No. PCT/US99/16242 (WIPO Publication WO 00-04192), the disclosure of which is hereby incorporated by reference in its entirety.

Composition of Matter:

The present invention relates to a universal linker composition suitable for gene expression arrays and related hybridization assays, including a nucleotide linking sequence which can be globally appended to the ends of a set of probes derived from mRNA transcripts of an analyte sample to produce a probe set where the probes have a common linker at one or both ends. These universal linker sequences are not complementary to the target sequences of the assay, and they provide binding sites to join the members of the probe set to common reporters. The universal linkers are also suitable for chemical cross-linking between bound linkers, so that probes, reporters, and any intermediate linking elements, can be pre-attached together and covalently bonded. The universal linkers additionally serve as universal primer binding sites for copying or amplifying the probe set.

The universal linkers of the present invention are suited to binding a variety of reporters that may have complementary linkers, particularly reporters such as the GeneTAG and TinkerTAG reporters, and arrays thereof, as referenced and described previously, where the GeneTAG reporters include linear labeled segments of duplex DNA that terminate in single stranded universal linkers and the TinkerTAG reporters that contain a structurally similar linear complex of labeled polynucleotides and that also terminate in single stranded universal linkers. These reporters can also form arrays of reporters joined end to end. The universal linkers are additionally suited to binding multi-linker elements, as referenced and described previously, may include one or more joined polynucleotides that form a probe linker at one end and two or more reporter linkers at the opposite end. The probes of the present invention may employ the universal linkers to bind reporters directly or indirectly, by virtue of binding multi-linkers to the probes, and binding reporters such as GeneTAGs or TinkerTAGs to the linkers of the multi-linkers.

The present invention additionally relates to a set of two or more universal linkers containing linker sequences which can bind two or more sets of probes to two or more different common reporters, either directly or via intermediate linkers, to provide different labeling to different sets of probes. These universal linker compositions include but are not limited to:

a. A first linker sequence 5'CTACGATACGATAGCGCCTAAGAGTAG (Seq. ID. No. 1) and its complement, known as the Red universal linker;

b. A second linker sequence 5'CCTAGACCTACGACATAGGTACCCTAC (Seq. ID. No. 2) and its complement, known as the Green universal linker;

c. A third linker sequence 5'CGTAGAACTAGCACGCTACGTACTAGG (Seq. ID. No. 3) and its complement, known as the Blue universal linker;

d. A fourth linker sequence 5'GGCTATCGCTACGTAGACTAGACCTAC (Seq. ID. No. 4) and its complement, known as the Orange universal linker.

The present invention relates to a probe set composition, called WRAP-Probes, for gene expression arrays and related hybridization assays, to provide common equivalent signaling per probe regardless of length, as contrasted with signaling bias which results from incorporating label along the length of each probe. This probe set includes a pool of modified cDNA probes copied in part from a sample of mRNA transcripts, but appended with terminal universal linkers, as in the prior WRAP-PROBE invention referenced and described previously, where each single stranded probe of the probe set contains a central target specific segment copied from a single mRNA transcript, and a universal linker located on a terminal end of the probe. The universal linkers provide binding sites to join common reporters to each probe, and they also provide primer binding sites to copy and amplify the probes. In a primary embodiment, to allow exponential amplification of the probes, probe sets are also made with universal linker sequences at both terminal ends. The universal linker sequences at both ends may be different or they may mirror one another, in which case the probe set has a common primer binding site and may be amplified with a single primer.

In another embodiment of the WRAP-Probe probe set, called Mini-WRAP-Probes, the probes are fragmented to provide multiple probes per mRNA transcript. Initially, the probe set of first strand cDNA probes is fragmented and then universal linkers are applied to one or both ends of the fragments to create a final probe set of multiple short probes having universal linkers. Thus, each transcript becomes a series of short or Mini WRAP-Probes with one or two terminal linkers, that provide greater signaling in two ways, by amplifying the multiple probe fragments, and by binding reporters to the linkers of the multiple probe fragments. Such fragmentation may be induced randomly by shearing, sonication, RNase, RNase-H, UNG, single strand cutting enzymes, and like treatments, or alternatively at specific sequences with restriction enzymes.

In other embodiments, two or more probe sets of WRAP-Probes or Mini-WRAP-Probes are provided, having probe sets that can be compared in the same assay, where the probes of each set have different universal linkers, and where the linkers provide binding sites for different multi-linkers, reporters or labeling that distinguish the probe sets from one another.

The present invention relates to a series of modified Poly-T Primer compositions for globally initiating the copying and conversion of mRNA transcripts into a set of WRAP-Probes. In the primary embodiment, the modified Poly-T Primer composition contains a polynucleotide in which the 3' end provides a poly-T primer segment to initiate RT polymerization and the 5' end provides a universal linker, wherein the linker can bind reporters to the probe. Alternatively, the Poly-T Primer composition has a poly-T end that also contains an anchor sequence to preferentially bind to the forward end of the poly-A segment of mRNA transcripts. In a primary embodiment, the anchor sequence takes the form 5'-poly-T,V, N-3', where poly-T is a series of thymidine bases, V is a variable base of adenine, cytosine or guanine, but not thymidine, and N is randomly any base. Other anchor sequences can be employed including the sequence 5'-poly-T, V. The Poly-T Primers are preferably made with about 12 to 20 thymidines in the poly-T segment.

In an additional embodiment, a Poly-T Primer composition is manufactured with a capture moiety such as biotin on the 5' end so that the probe units can be captured with magnetic beads or other methods and retained, purified, treated, or re-used to copy the original probe set. In other embodiments, the modified Poly-T Primer is manufactured with labeling elements attached, or alternatively, one or more reporters are pre-attached prior to use. Alternatively, the modified Poly-T Primer is constructed with a multi-linker pre-attached, wherein reporters can be attached or pre-attached to the multi-linker. Such reporters can include GeneTAGs, TinkerTAGs or arrays of such reporters. Additionally, a set of two or more Poly-T Primer compositions are provided, that include different universal linkers, multi-linkers, reporters and label or labeling precursor so that each resulting probe subset can be distinguished by different signaling.

The present invention also relates to a series of adapter compositions for providing a second universal linker to the probe sets. One product embodiment is a sequence specific adapter composition, called a Specific Adapter that is typically ligated to the 3' end of a DNA probe segment. This adapter product contains two polynucleotides joined together by complementary bases, where the complementary bases are a set of universal linker sequences, and where one end contains an additional single-stranded overhang, typically of 1 to about 6 bases, that can specifically bind to the terminal end of a probe that has been cut with a specific restriction enzyme. These Specific Adapters are also manufactured as a set of two or more such adapter products to allow sample comparisons, where each adapter in the set has a different universal linker sequence that can bind different reporters or multi-linkers.

The present invention also relates to a series of random adapter compositions for providing a second universal linker to the probe sets. One embodiment is a Random Adapter product that is typically ligated to the end of a DNA probe segment. The Random Adapter composition contains two polynucleotides joined together by complementary bases, where the complementary bases are a set of universal linker sequences, and where one end has an additional single-stranded overhang of random bases, typically of 1 to about 6 random bases. Such random sequences, which are also called degenerate sequences, are typically represented as an "N" in sequence descriptions and are chemically synthesized by providing alternatively and randomly: an adenine (A), thymidine (T), cytosine (C) or guanine (G), at each position in the random sequence. A set of two or more Random Adapters are also provided by the invention to allow sample comparisons, where each adapter in the set has a different universal linker sequence. Another product embodiment is a homopolymeric adapter composition that is also typically ligated to the end of a DNA probe segment, but in this case, the 3' end of the probes are first extended with a poly-C or poly-G sequence. The homopolymeric adapter product contains two polynucleotides joined together by complementary bases, where the complementary bases are a set of universal linker sequences, and where one end contains an additional single-stranded overhang of poly-C or poly-G bases. The homopolymeric adapter binds to a complementary tail of poly-G or poly-C sequences that is previously appended to the probes using terminal transferase and a sole nucleotide. A set of two or more homopolymeric adapters is also provided to allow sample comparisons, where each adapter in the set has a different universal linker sequence. In alternate product embodiments, the Specific Adapter, the Random Adapter or the Homopolymeric Adapter is labeled.

The present invention also relates to a series of extender products for providing a second universal linker to the probe sets. One random extender composition, called a Random End-Linker, binds to the end of a probe at random and extends its sequences as a copy of the linker sequences of the extender. This extender includes a single-stranded polynucleotide with a 5' end containing universal linker sequences, and a 3' end containing random sequences, preferably about 4 to about 10 random sequences (also called degenerate sequences). In a preferred embodiment, the Random End-Linker is chemically modified on the 3' end to block or prevent polymerase extension of that end, where one modification practiced is to add a carbon spacer to the 3' end. Consequently, this product will not forward copy. The present invention provides a set of two or more Random End-Linker products to allow sample comparisons, where each composition in the set has a different universal linker sequence. An alternate extender product of the present invention is a homopolymeric extender that includes a single-stranded polynucleotide with a 5' end containing universal linker sequences, and a 3' end containing poly-C or poly-G sequences, preferably of about 5 to about 15 poly-C or poly-G sequences. The homopolymeric extender binds to a tail of poly-G or poly-C sequences that is previously added to the 3' end of a probe by terminal transferase. The present invention provides a set of two or more homopolymeric extender products to allow sample comparisons, where each composition in the set has a different universal linker sequence.

The present invention relates to a universal linker-primer-reporter composition, called a ChipTAG, which includes a single-stranded polynucleotide with universal linker sequences that is manufactured with a label or labeling precursors attached and where the linker sequences provide both a primer function for DNA polymerase activity and a linker function to bind the labeled ChipTAG as a reporter to a probe. Additionally, two or more sets of ChipTAG compositions are provided to allow sample comparisons, where the ChipTAGs may differ from one another in both their linker sequences and in their pre-attached label or labeling precursors, and where different labeling is provided to different probe sets.

Method:

The present invention relates to a series of methods for gene expression arrays and related assays that enable the manufacture and application of the related composition of matter inventions described above. These methods attach common reporters to the ends of a probe set, typically by virtue of universal linkers created at one or both ends of the probes, to give each probe in the set an essentially equivalent signaling level, thereby enabling a more effective count of the number of different transcripts in the original RNA sample. However, these methods also allow internal labeling of the probes by standard methods, either additionally or alternatively. Since some of the methods truncate the lengths of the probes so that their size variation is reduced or eliminated, these methods can additional enable the normalization of signaling between probes even when they are internally labeled. These methods can additionally amplify the probe sets globally by virtue of the terminal universal linkers so that exponential amplification procedures such as PCR or related methods can be practiced if the probes have linkers at both ends, and so that linear amplification procedures can be practiced if the probes have one linker.

The present invention relates to a general method to make and apply WRAP-Probe probe sets for gene expression analysis, where more accurate quantitative detection is achieved by attaching common reporters to one or both ends of each probe, this method comprising:

a. Providing RNA from a tissue sample;
b. Making cDNA probes from the RNA transcripts with universal linkers at one or both ends;
c. Hybridizing the cDNA probes to an array or series of gene specific targets;
d. Joining reporters to the cDNA probes; and
e. Detecting reporters to determine the expression of genes in the tissue sample.

In its most elementary embodiment, the WRAP-Probe method produces a probe set with a single linker or reporter end, comprising:

a. Hybridizing a modified poly-T primer with a universal linker to the mRNA transcripts;
b. Polymerizing full or partial first strand cDNA copies of the transcripts to form one linker probes with a common 5' signaling end.

This method is illustrated in FIG. 1 where step 1 shows the use of the poly-T primer to make a first strand cDNA probe with a 5' universal linker, step 2 shows the binding of the probes to the cDNA chip, and step 3 shows the binding of GeneTAGs to the linkers of the probes.

This one-linker WRAP-Probe method can bind multi-linkers and or reporters to the 5' universal linker affixed to the probes, including but not limited to GeneTAGs, TinkerTAGs or reporter arrays thereof, as well as ChipTAGs or commercially available reporters such as the bDNA reporters of Chiron Corp. [Urdea et al. (U.S. Pat. No. 5,124,246)] or the Dendrimer reporters of Polyprobe, Inc. [Nilsen and Prensky, (U.S. Pat. No. 5,487,973)], if such reporters were re-manufactured with nucleotide linking sequences that corresponded to the universal linkers of the WRAP-Probes of the present invention. Alternatively, poly-T primer compositions are provided that have multi-linkers and or reporters and or label pre-attached, where a second step is not required to hybridize these signaling elements to the probes after the probes are hybridized to the targets of the expression assay. The present invention also provides different one-linker probe sets, based upon differences in linker sequence, labeling and reporter attachment so that probe set comparisons can be performed on the same assay.

The most common form of the WRAP-Probe method is double-linker probes and the general method to make and apply double-linker WRAP-Probe probe sets comprises:

a. Hybridizing the poly-T primer composition with a universal linker to the mRNA transcripts;
b. Polymerizing full or partial first strand cDNA copies of the transcripts to form an initial probe set with a common 5' first universal linker;
c. Affixing a second universal linker to the 3' end of the probes to make a final double-linker probe set.

In the above and subsequent double-linker WRAP-Probe methods, each probe strand has a 5' and a 3' universal linker, wherein the 5' end is already suitable for effective end-to-end binding to the complementary 5' single stranded linker end of a typical GeneTAG, TinkerTAG or multi-linker. However, the 3' end is less suitable for such end to end binding. Therefore, based on procedures of the WRAP-PROBE method of the prior invention, the 3' ends of the probe set of the present invention are optionally modified by applying and cross-linking an additional polynucleotide linker that reverses the polarity of the probe end to provide a 5' universal linker end. (See Example 3) To achieve this, the universal linker sequences are typically designed with one or more 5'TA sequences to enable the application of PUVA cross-linking, wherein free psoralen plus UV blacklight treatment covalently joins contra-lateral thymidine bases. Alternatively, a subset of GeneTAG reporters can be pre-made with 3' vs. 5' end linkers in a similar manner, or TinkerTAGs can be made directly with 3' end linkers.

The double-linker WRAP-Probe method provides several sub-methods to alternatively apply the second universal linker to the 3' ends of the first strand cDNA probes.

The first primary double-linker sub-method of the WRAP-Probe method employs restriction enzyme cutting and ligation of the Specific Adapter product to shorten the probes and form universal linkers at both ends, wherein the modifications comprise:

a. Providing the Poly-T Primer composition with a capture moiety, such as biotin, at the 5' end;
b. Polymerizing first strand cDNA and then second strand cDNA to form double stranded cDNA with a 5' first strand universal linker and a capture moiety.
c. Cutting the double stranded cDNA products with a restriction enzyme;
d. Selectively capturing the terminal 5' probe fragments of first strand cDNA by virtue of the capture moiety, using strepavidin-coated magnetic beads or similar capture techniques;
e. Joining a Specific Adapter to the cut 3' end of the captured probe fragments to append a 3' second universal linker and create a final double-linker WRAP-Probe probe set, wherein the probe set is denatured and applied to gene expression assays.

Figure 2:
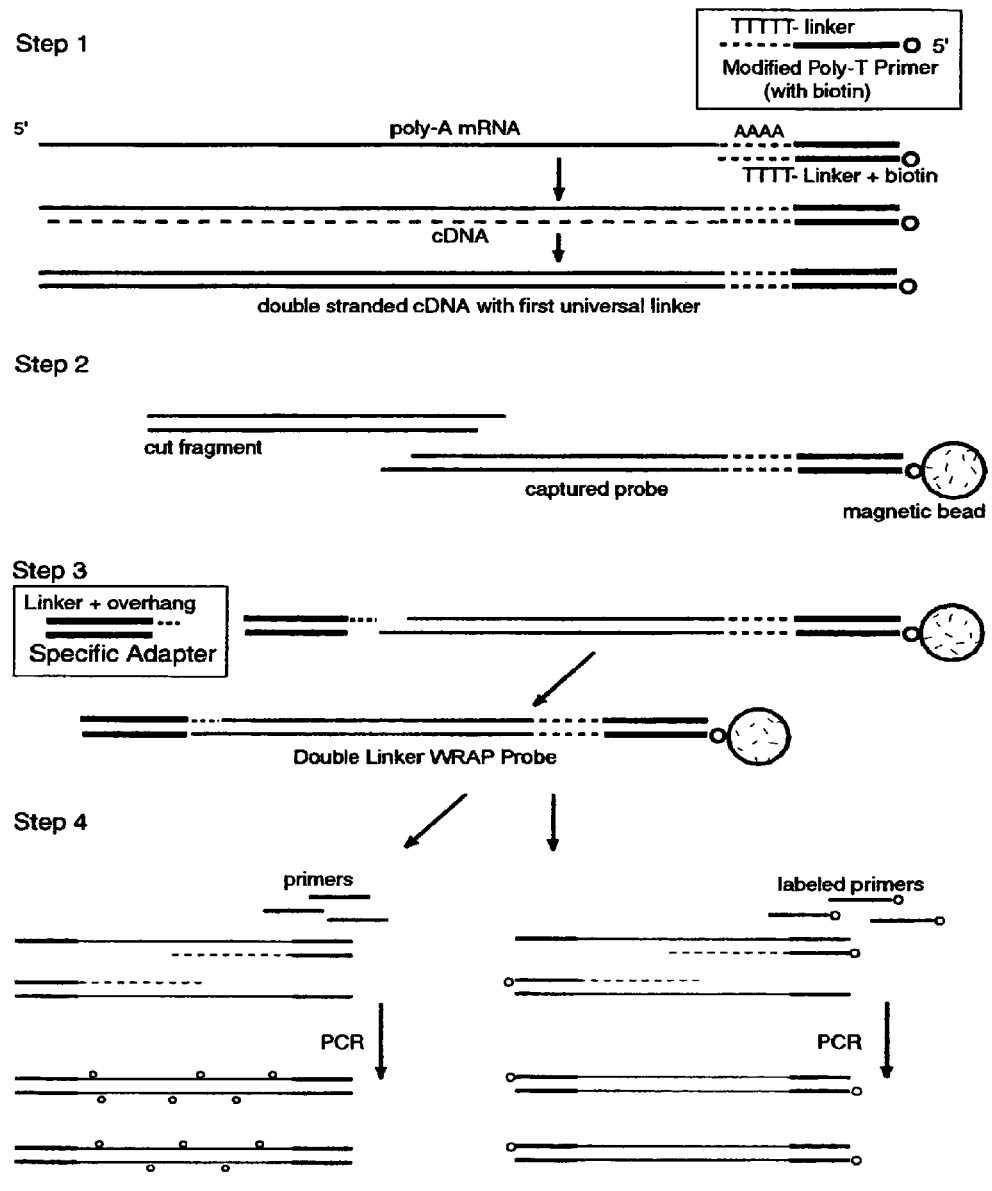
FIG. 2: Amplified WRAP-Probe method. Sub method One: Restriction cutting and adapter ligation. Step 1 depicts the conversion of mRNA into double stranded cDNA with one universal linker by copying the mRNA with RT and a modified poly-T primer, and by polymerizing a second strand with DNA polymerase and RnaseH. Step 2 depicts cutting the probes with a restriction enzyme and capturing them with magnetic beads via the capture moiety, such as biotin. Step 3 depicts ligating the Specific Adapter to the cut ends of the probe to provide a second universal linker and to form double-linker probes. Step 4 depicts PCR amplification of the probes, wherein the probes are either labeled internally with labeled bases or labeled on the end using labeled primers eg. ChipTAGs. Additionally, GeneTAG or TinkerTAG reporters can be added to the probes after they are bound to the cDNA chips.
Figure 7:
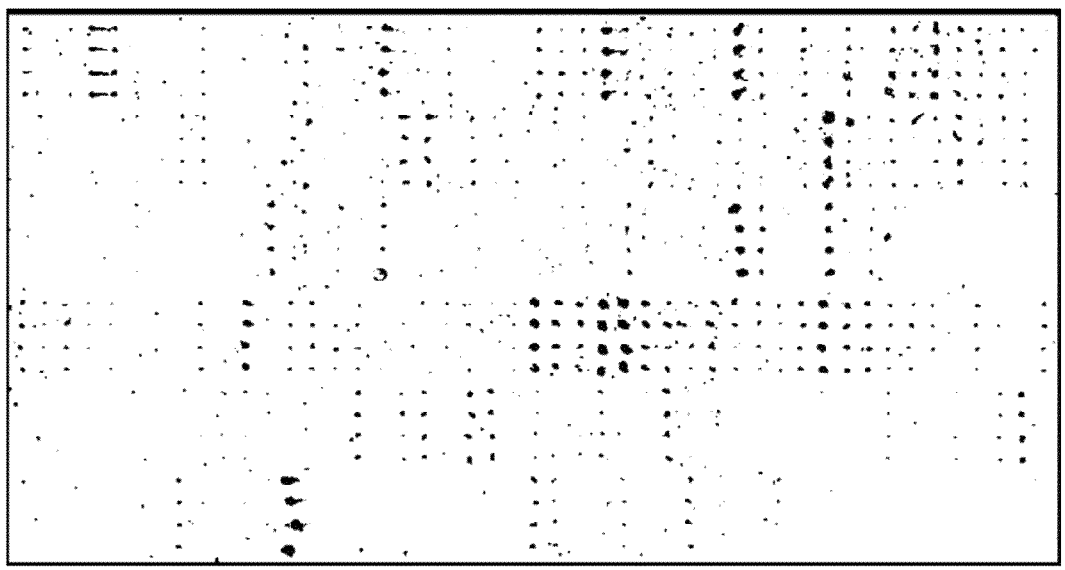
FIG. 7: Image from Example 3.
Figure 8:
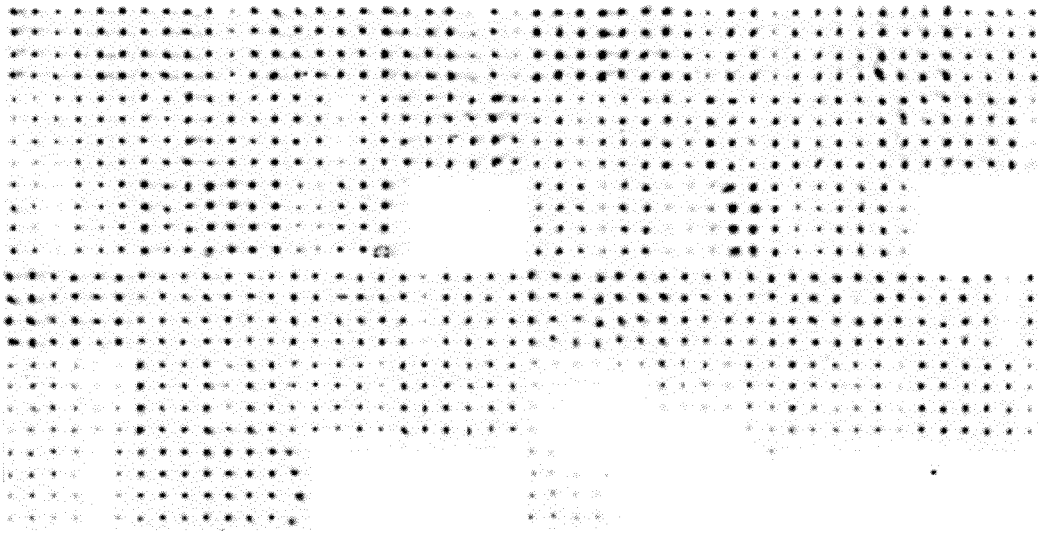
FIG. 8: Image from Example 3.
Figure 9:
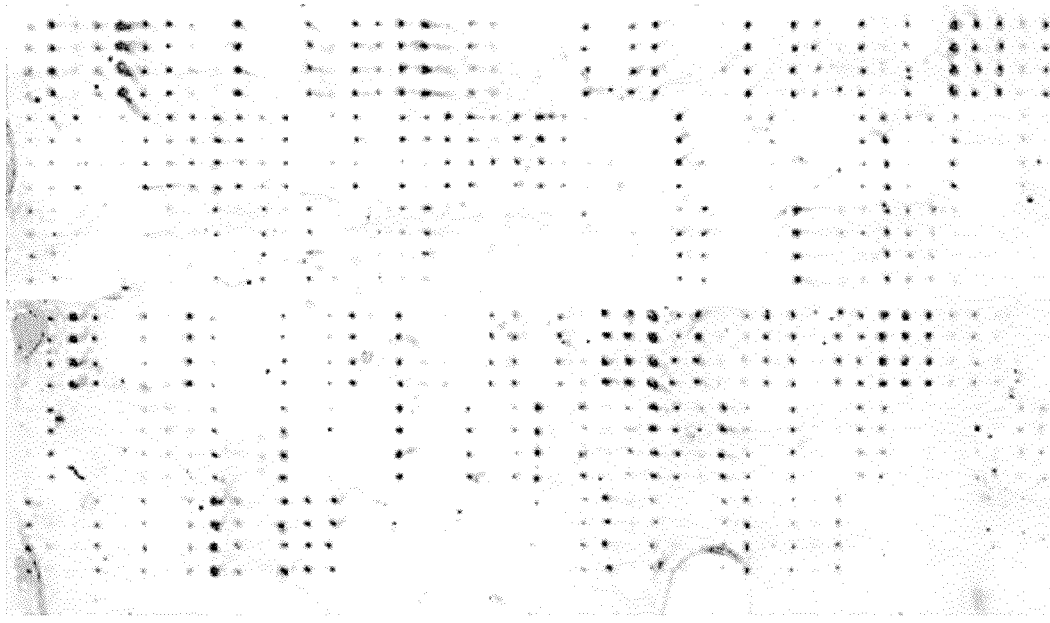
FIG. 9: Image from Example 4.

This method was used to create the double linker probes of FIGS. 7, 8 and 9 although those probes were amplified by PCR as well. FIG. 2 illustrates this method in step 1, where the mRNA is converted to double stranded cDNA with one universal linker by copying the mRNA with RT and a modified poly-T primer, and by then polymerizing a second strand with DNA polymerase and RNase H. Step 2 depicts cutting the probes with a restriction enzyme and capturing them with magnetic beads. Step 3 depicts ligating the Specific Adapter to the 3' cut ends of the captured probes to append a second universal linker and to form double-linker probes. This figure also depicts a further step in Step 4 that is not a part of the above method. In Step 4 the probes are amplified by PCR amplification and either labeled internally with labeled bases or labeled on their ends using a ChipTAG labeled primer.

In a preferred embodiment of the above method, two or more restriction enzymes are employed in separate probe aliquots using Specific Adapters matched to the cut sites. This modification is provided to ensure that no gene is unrepresented in a detection sample since the use of one restriction enzyme may cause a particular gene to always be cut at a site too close to the poly-A end of the transcript to produce a viable probe. With this modification, the separate probe aliquots are then mixed and applied together for analysis.

The second primary double-linker sub-method of the WRAP-Probe method employs the new random extender product, called a Random End-Linker, to form a second universal linker on the 3' end of the probes, where the extender is applied with a new thermal cycling procedure called Back-Tagging. This method comprises the following modifications:

a. Providing first strand cDNA probes with a 5' universal linker;
  b. Denaturing and removing the RNA;
  c. Repeatedly hybridizing the random extender to the probes under rapid thermal cycling conditions similar to PCR, wherein high temperature DNA polymerase and nucleotides are provided along with repeat cycles of high temperature denaturing, low temperature annealing, and moderate temperature but brief extension, to bind the random extender to the 3' ends of the probes via the random segment and to selectively extend the 3' ends of the probes using the universal linker segment of the random extender as a sequence template, to create a second universal linker on the 3' ends of the probes, to form a final double-linker probe set.

Figure 3:
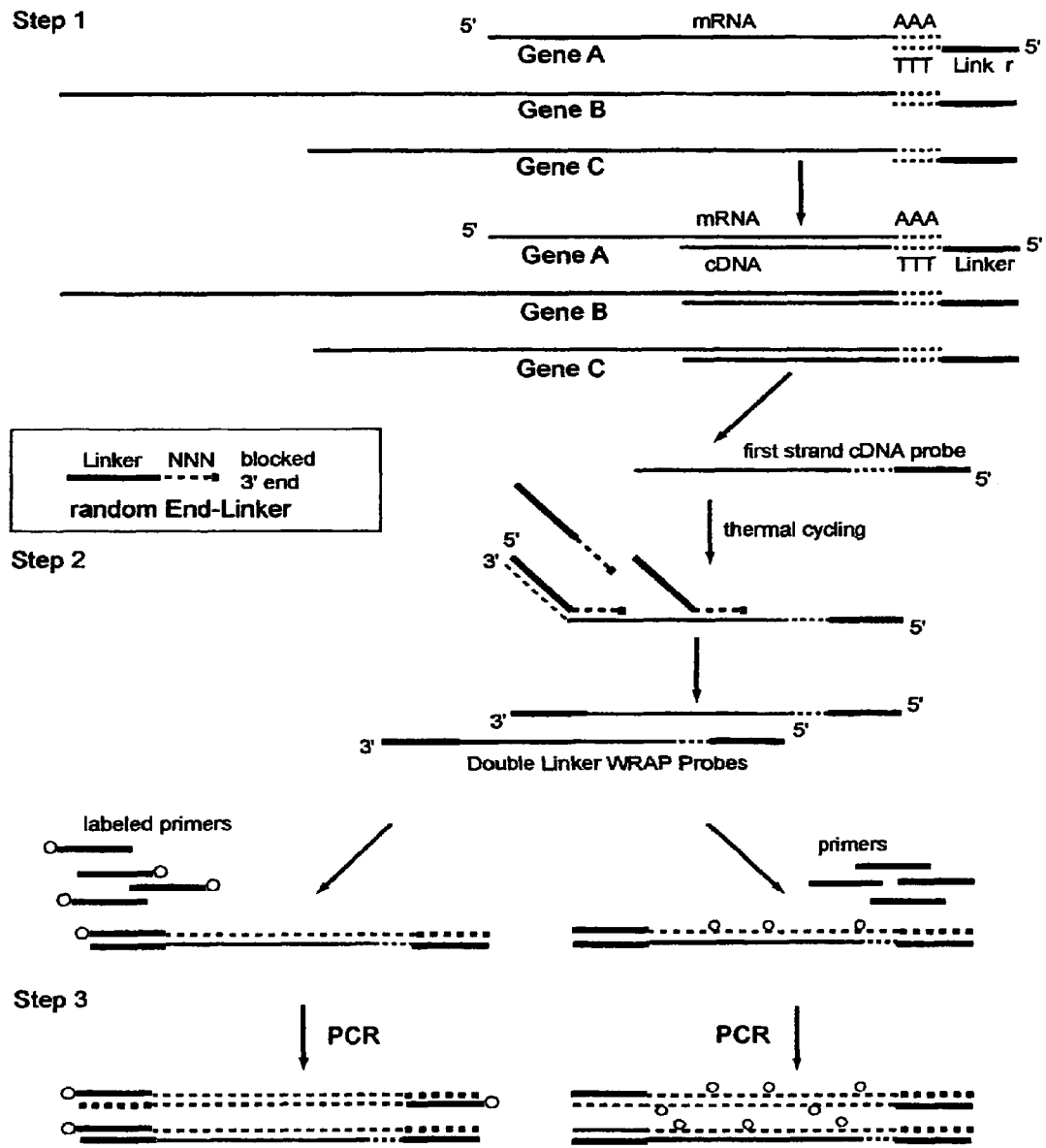
FIG. 3: Amplified WRAP-Probe method. Sub method Two: Applying Short RT and the Random End-Linker to make Double-Linker cDNA probes. Step 1 depicts how the mRNA is converted to first strand cDNA probes with one universal linker and it further depicts the short RT procedure where different transcripts of different lengths are stopped short at approximately the same length. Step 2 depicts binding of the random extender, called the Random End-Linker, to the probes during multi-cycle thermal cycling where the extender binds but does not prime if it binds anywhere along the probes except the 3' end, and where it extends the 3' end with a universal linker when it binds to the 3' end. Step 3 depicts the further step of amplifying the double linker probes by PCR with labeling incorporated either in the bases or by using ChipTAG primers. Labeling can be applied in both ways to the probes, and additional labeling can also be provided by adding GeneTAGs or TinkerTAGs to the universal linkers of the probes.
Figure 10:
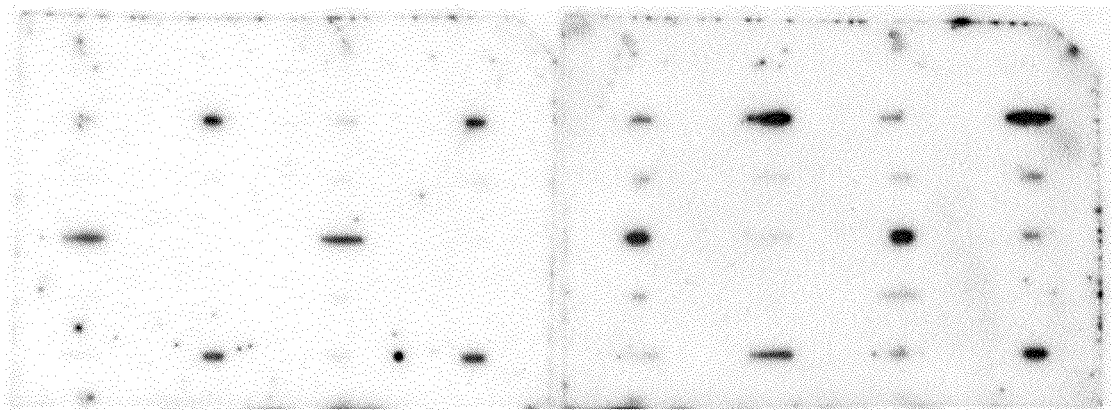
FIG. 10: Images from Example 6. These images demonstrate the use of Amplified WRAP-Probe Sub method Two which employs the Short RT and Random End-Linker procedures followed by PCR amplification of the probes. In this case, gene expression analysis is shown with P-32 labeled probes that are hybridized to membrane-based arrays. Expression profiling is demonstrated that distinguishes between control and IL-13 treated monocyte samples based upon starting with only 1 microgram of total RNA per sample.

This method was employed to create the double linker probes of FIG. 10 although those probes were also amplified by PCR. FIG. 3 illustrates this method in step 1 and step 2, where step 1 depicts how the mRNA is converted to first strand cDNA probes with one universal linker, although this illustration also depicts the short RT procedure where the first strand copy is stopped short. Step 2 depicts binding of the random extender composition, called the Random End-Linker, to the probes during multi-cycle thermal cycling where the extender binds but does not prime if it binds anywhere along the probes except the 3' end, and where it extends the 3' end with a universal linker when it binds to the 3' end. Step 3 of FIG. 3 depicts a further step, not a part of this specific method, where the double linker probes are amplified by PCR with labeling incorporated in the bases or by using ChipTAG primers.

Although the Back-Tagging procedure employs thermal cycling and high temperature polymerase reagents common to the PCR method, it does not practice the PCR procedure to copy or exponentially amplify the products since the 3' end of the Random End-Linker is preferably blocked and cannot serve as a primer. Consequently, when the temperature is lowered each cycle to anneal the Random End-Linker products to the probes, these extenders will bind at random but will not function unless they happen to bind to the 3' end of the probe fragment. Indeed, the annealing step can be practiced at lower temperatures than would be employed for PCR since the goal is to force as many Random End-Linkers onto the probe strand as possible to increase the chances that one will bind to the 3' end. Since, the extenders will come off again each high temperature cycle in an unmodified state they will be reused on the next annealing cycle whereupon they might again bind to the 3' end. Once they do bind to the end of the probe fragment, it will extend 3' by polymerization using the linker sequences of the Random End-Linker as a template to form a 3' universal linker. When it binds anywhere else along the probe, the blocked end of the random end-linker prevents copying any portion of the first strand fragments. Thus, the formation of spurious fragments is avoided and the rapid use of nucleotides and enzyme is prevented. Therefore, thermal cycling can be continued for hundreds of cycles to effectively apply second universal linkers to the first strand probes. This principle and method has multiple uses in the present invention and for other applications.

The third double-linker sub-method of the WRAP-Probe method employs the Random Adapter product to append the second universal linker, comprising the following modifications:

a. Providing first strand cDNA probes with a 5' universal linker;
  b. Denaturing and removing the RNA;
  c. Joining the random adapter to the 3' end of the probes to append a second universal linker, to create a final double-linker probe set.

Figure 4:
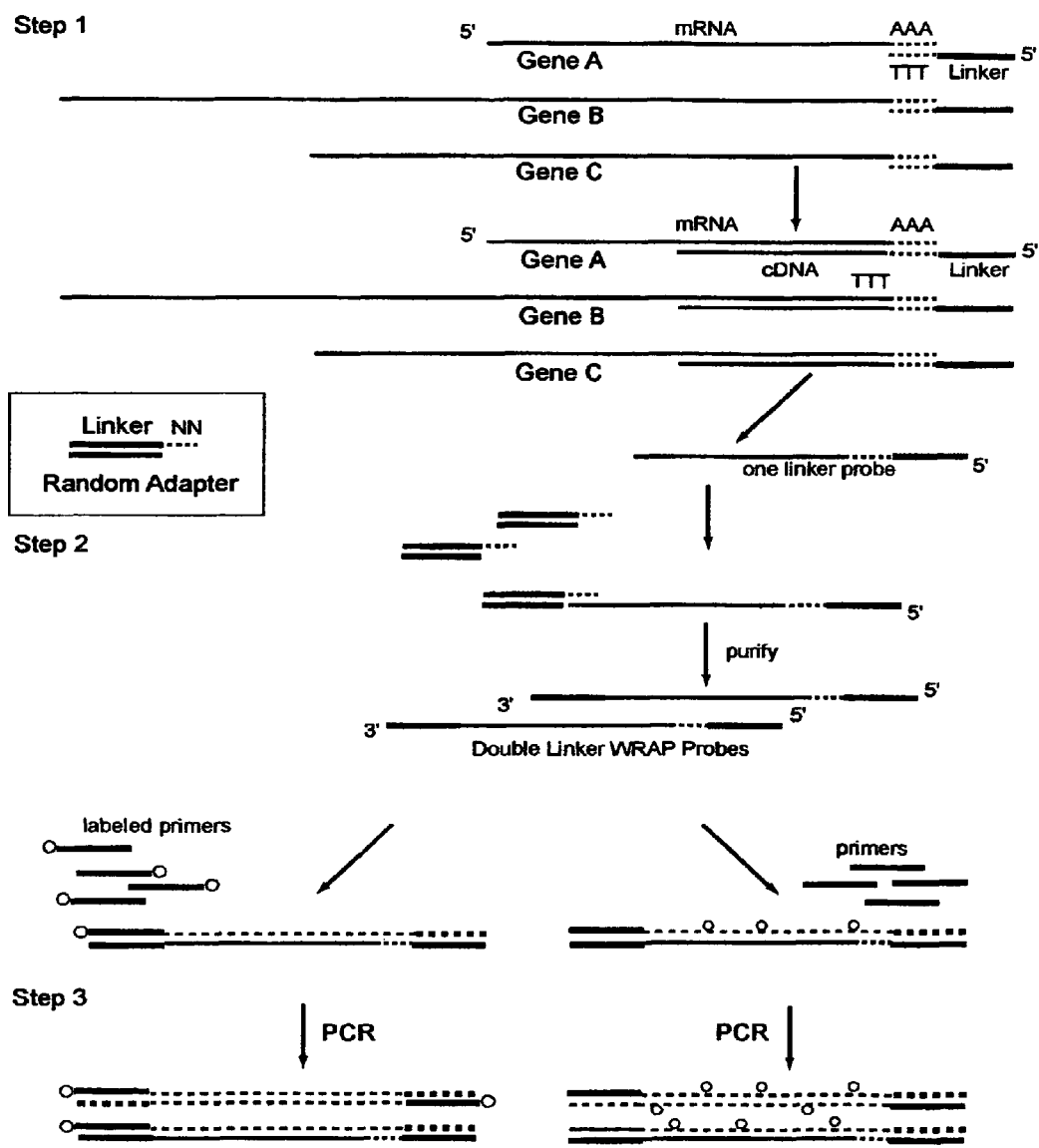
FIG. 4: Amplified WRAP-Probe method. Sub method Three: Applying Short RT and Random Adapter to create double-linker probes. Step 1 depicts how the mRNA is converted to first strand cDNA probes with a 5' universal linker by polymerizing cDNA with a modified poly-T primer, and it further depicts the short RT procedure where different transcripts of different lengths are stopped short at approximately the same length. Step 2 depicts binding of the random adapter by ligation to the 3' end of the probes to form double linker probes. Step 3 depicts amplifying these double linker probes by PCR with labeling incorporated either in the bases or on the ends by using ChipTAG primers.
Figure 11:
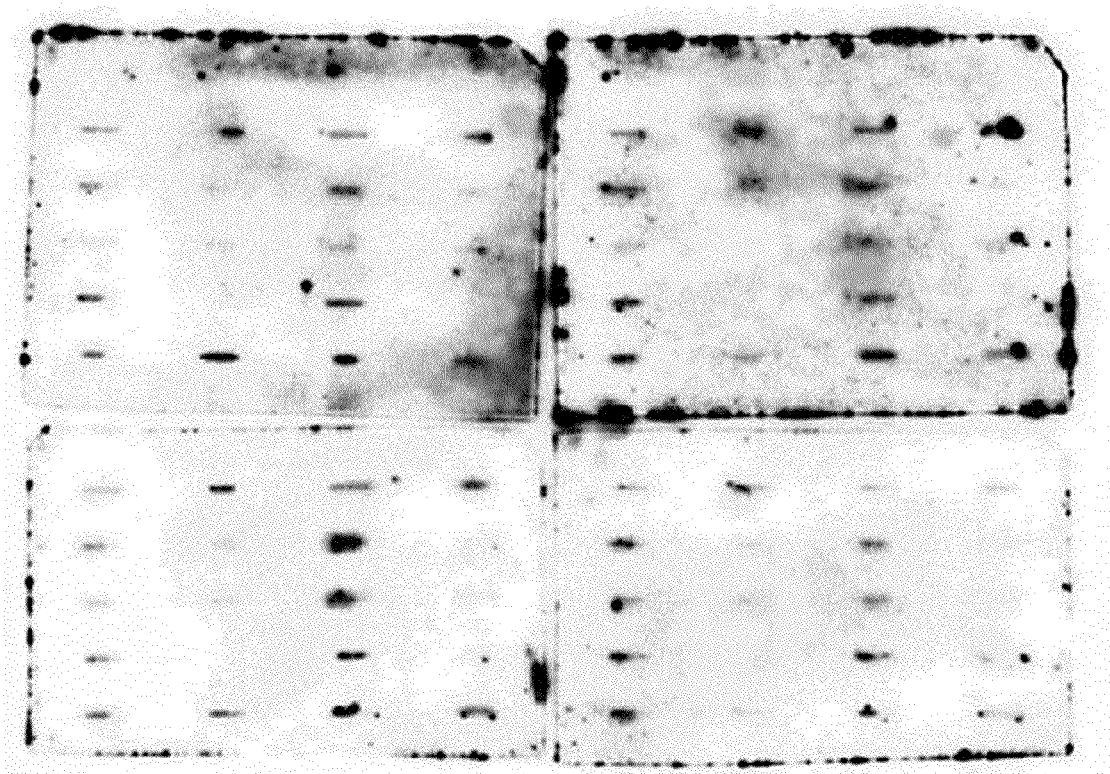
FIG. 11: Images from Example 7. These images shows P-32 labeled probes hybridized to membrane-based arrays using the Amplified WRAP-Probe Sub method Three that employs the Short RT procedure, the ligation of Random Adapters, and then PCR amplification of the probes. Expression profiling is depicted for Short RT using different RT exposure times of 2 min, 5 min, 10 min and 20 min. The shorter RT exposure times give better results than longer exposures.

This method was used to create the double linker probes of FIG. 11 although those probes were amplified by PCR as well. This method is illustrated in step 1 and 2 of FIG. 4 where step 1 depicts how the mRNA is converted to first strand cDNA probes with one universal linker, although this illustration also depicts the short RT procedure where the first strand copy is stopped short. Step 2 depicts binding of the random adapter by ligation to the 3' end of the probes to form double linker probes. Step 3 of FIG. 4 depicts a further step, not a part of this specific method, where the double linker probes are amplified by PCR with labeling incorporated either in the bases or on the ends by using ChipTAG primers.

The fourth double-linker sub method of the WRAP-Probe method employs homopolymeric tailing and application of the homopolymeric adapter product to append the second universal linker, comprising the following modifications:

a. Providing first strand cDNA probes with a 5' universal linker;
  b. Denaturing and removing the RNA;
  c. Extending the 3' end of the probe fragments with a homopolymeric tail of poly-C or poly-G sequences using terminal transferase and one nucleotide;
  d. joining a matching homopolymeric adapter to the homopolymeric tail on the 3' ends of the probes to append a second universal linker and to create a final double-linker probe set.

Alternatively the homopolymeric extender can be substituted in the above procedure wherein this modification comprises the steps of:

a. providing first strand cDNA probes with a 5' universal linker and a 3' homopolymeric tail of poly-C or poly-G sequences;
  b. joining a matching homopolymeric extender to the homopolymeric tail on the 3' ends of the probes and polymerizing a 3' extension, wherein the universal linker segment of the extender provides a sequence template for extending the 3' end of the probes with a second universal linker sequence, to create a final double-linker probe set.

Figure 5:
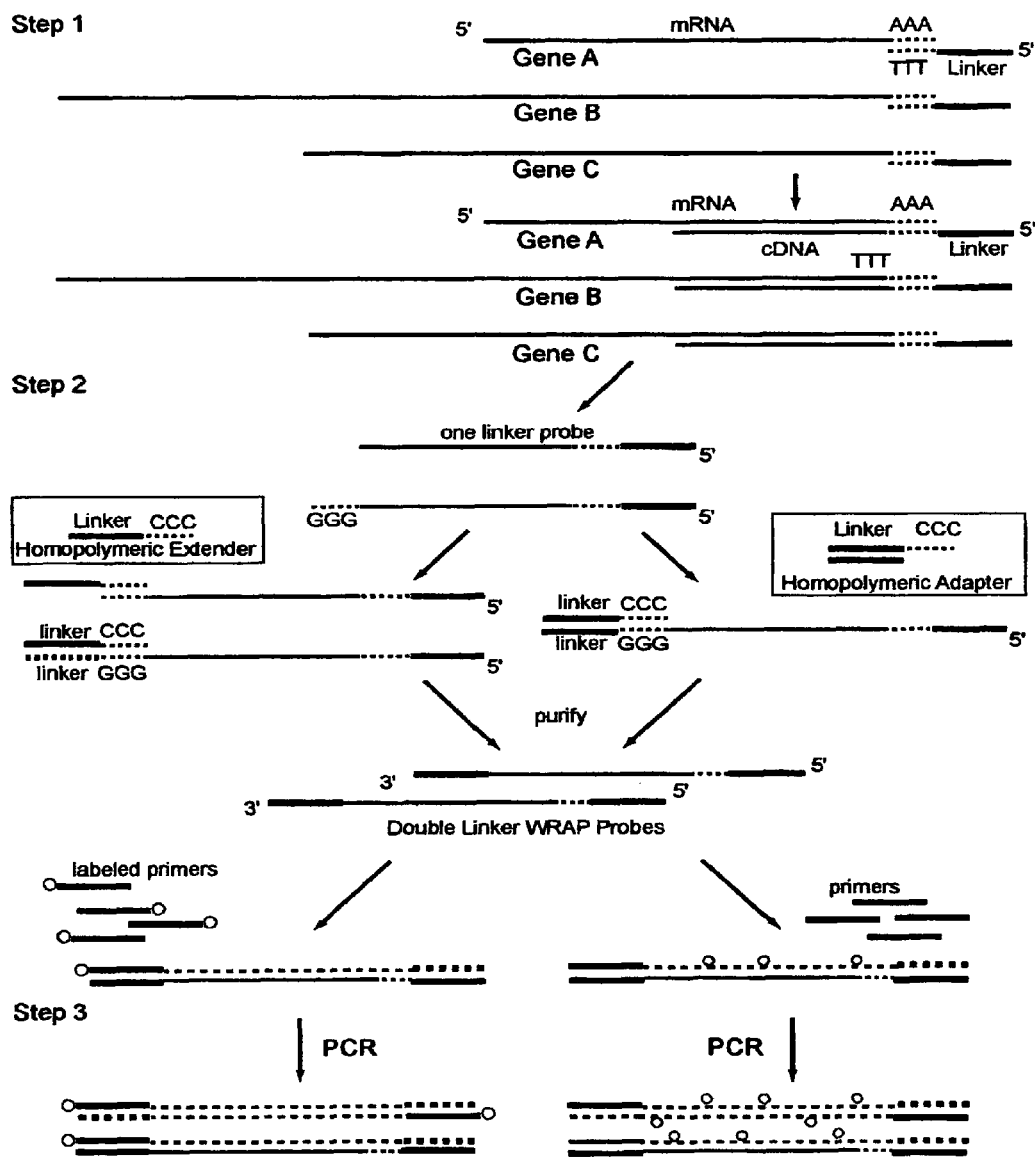
FIG. 5: Amplified WRAP-Probe method. Sub method Four: Short RT and homopolymeric. These methods use either homopolymeric adapters or extenders. Step 1 depicts how the mRNA is converted to first strand cDNA probes with one universal linker, and it additionally depicts the short RT procedure where the first strand copy is stopped short for all transcripts. Step 2 depicts alternatively either the binding of the homopolymeric extender on the left or the homopolymeric adapter on the right to extend or append the second universal linker unto the 3' end of the probes to form double linker probes. Step 3 depicts the further step of amplifying these double linker probes by PCR with labeling incorporated either in the bases or on the ends by using to ChipTAG primers.

These methods using homopolymeric adapters or extenders are illustrated in step 1 and 2 of FIG. 5 where step 1 depicts how the mRNA is converted to first strand cDNA probes with one universal linker, although this illustration also depicts the short RT procedure where the first strand copy is stopped short. Step 2 depicts alternatively either the binding of the homopolymeric extender on the left or the homopolymeric adapter on the right to extend or append the second universal linker unto the 3' end of the probes to form double linker probes. Step 3 of FIG. 3 depicts the further step of amplifying these double linker probes by PCR with labeling incorporated either in the bases or on the ends by using ChipTAG primers.

In preferred embodiments of the WRAP-Probe method, the RT copying of the mRNAs is intentionally truncated by greatly reducing the duration of exposure to the enzyme to purposefully produce very short RT products, generally less than 1000 bases in length and preferably less than 500 bases. Brief RT exposure times of several minutes or seconds are herein employed as contrasted with one hour or more of RT exposure by standard cDNA chip labeling methods. This radical modification of the RT protocol, called Short-RT, results in first strand cDNA probe components that are randomly and arbitrarily short such that pre-existing size differences between genes and gene transcripts are effectively eliminated, wherein the method normalizes the lengths of the probes, improves the ability to affix random end-linkers to the probe components, improves the kinetics of probe binding to the expression assay, and allows the internal labeling of the probes as a supplement to reporter binding without to reintroducing bias in signaling between genes due to inherent differences in transcript length. Short probes also provide more efficient amplification of the double-linker probes by exponential procedures such as PCR.

The Short RT procedure is generally employed in conjunction with the double-linker WRAP-Probe methods described above that don't require a specific cut site to apply a second linker, wherein the modified steps comprise:

a. Hybridizing a modified poly-T primer with a universal linker to the mRNA transcripts;

b. Polymerizing truncated first strand cDNA copies of the transcripts by abruptly terminating RT polymerase progression by time, to form an initial set of shortened probe fragments with a 5' universal linker;

c. Applying a second universal linker to the 3' ends of the shortened probes to create a final double-linker probe set.

In preferred embodiments, the Short RT procedure is improved or augmented by additional treatments, including but not limited to cold, heat, alkali, enzymes such as RNase and RnaseH, single stranded cutting enzymes, UNG, shearing, sonication or like treatments.

Amplified WRAP-Probes Methods:

The present invention also relates to a modification of the double-linker WRAP-Probes method, called the Amplified WRAP-Probes method, to provide improved assay sensitivity, wherein the universal linkers affixed to both ends of the probes are used as primer sites to globally and exponentially amplify the probe set, the amplification method comprising:

a. Providing a double-linker probe set with universal linker-primer sites on both ends;

b. Providing primers that match or complement the universal linker-primer sequences of the probes;

c. Amplifying the set of probes exponentially by PCR or related processes;

d. Denaturing and hybridizing the probes to an array or series of gene specific targets.

In the Amplified WRAP-Probes methods, probe labeling may be incorporated enzymatically during PCR either by using bases conjugated directly with labeling agents, such as Cy3 or Cy5 fluorescent compounds, or by incorporating bases with labeling haptens such as amines, biotin or digoxygenin, whereupon labeling is added to the haptens in a second processing step. In Examples 2, 3 and 5 below such probe labeling employed direct labeling with Cy3-dCTP or Cy5-dCTP, or indirect labeling with amino-allyl dUTP (Sigma) to make amino-conjugated bases, whereupon the probes are then coupled to Cy dyes using Cy3 or Cy5 mono-functional reactive dye packs (AP Biotech).

In further embodiments of the Amplified WRAP-Probes method, the probe sets are alternatively or additionally labeled via the primers, such as the linker-primer-reporter products called ChipTAGs that comprise labeled universal linkers. In Example 4 below the ChipTAG primers are manufactured with Cy5 on their 5' ends and provide the sole labeling for the probes. Since ChipTAGs can be labeled more efficiently than probes can be labeled internally, ChipTAG labeling can fully substitute for internal enzymatic labeling with just a few steps of probe amplification. By labeling the ends of the probes, ChipTAGs also improve quantification of signaling per probe.

Alternatively or additionally, the probes may be labeled by binding GeneTAG or TinkerTAG reporters to the universal linkers of the probes, generally after the probes are hybridized to the targets on the expression assay, such as in the Examples 2 and 3 below which employ GeneTAGs labeled directly with Cy5-dCTP bases. Additionally, multi-linkers as described previously could be applied to the probes to increase the number of reporters bound, and furthermore, the labeled primers, called ChipTAGs can be added to the probes before or after the probes are hybridized to the targets, so that any matching linker ends not having label will bind ChipTAGs and add label. This was practiced in Example 4 where an aliquot of ChipTAGs was added back to the probes denatured and applied to the expression arrays, thereby adding a second ChipTAG to the 3' end of each single stranded probe.

In a further embodiment of the Amplified WRAP-Probes method, the modified poly-T primer product with a 5' capture moiety is employed to allow high fidelity re-amplification of the probe set. In this embodiment, the original double-linker probe products have a 5' capture moiety and they are then captured, separated and retained, so that these original copies may be selectively reused for additional amplifications of the probe set, such as in Examples 3 and 4 below. This procedure can be applied to any of the double-linker probe methods to selectively capture, retain and reuse the first strand cDNA probes with linkers on both ends to amplify and re-amplify the first copy of the probes from the mRNA transcripts. This procedure inhibits or prevents any bias that may be introduced by sequence copying errors during amplification or by any random "Monte Carlo" variations in relative amplification that may occur in the very low frequency transcripts.

To improve amplification efficiency and to reduce or eliminate amplification bias, additional embodiments of the Amplified WRAP-Probes methods are further modified by creating shortened double-linker WRAP-Probes, generally by employing the restriction cutting or the Short RT procedures describe above, wherein the probes are generally reduced to less than 1000 bases and preferably to less than 500 bases. Examples 3 and 4 below employ restriction cutting to reduce the probe size for more effective amplification. Examples 5, 6 and 7 employ Short RT to reduce probe length, wherein Examples 5 and 6 additionally employ the Random End-Linker and rapid thermal cycling with the Back-Tagging procedure to provide the second linker needed for PCR amplification, and wherein Example 7 additionally employs the Random Adapter to provide the second universal linker needed for amplification. Run on a gel, these amplified products form smears of shortened probes in the size ranges described above.

Additional embodiments of the Amplified WRAP-Probes method create and employ two or more sets of double-linker WRAP-Probes which differ in labeling, wherein multiple probe sets may be compared in the same assay.

The various WRAP-Probe methods described above, including the single and double-linker methods, the amplified methods, and the fragmented probes methods are additionally or alternatively provided direct signal amplification by applying various reporters to the universal linkers of the probe sets, wherein such reporters include, but are not limited to, GeneTAGs, TinkerTAGs, arrays thereof, and multi-linker and reporter constructs thereof as previously described. In Examples 2 and 3 below the probes labeled with Cy3 fluorescence are applied to the expression arrays and then one or more GeneTAGs labeled with Cy5 fluorescence are added to each probe in a second hybridization. Therefore, the labeling provided by the probes and the added labeling provided by the GeneTAGs is evident since the two dyes are separately excited, scanned and detected in different channels as independent signals.

Other commercial labeling products may also be applied to the universal linkers of the probe sets such as the bDNA products of Chiron Corp., or the dendrimer products of Polyprobe, Inc. if such products can be prepared with complementary universal linker ends. The present invention also embodies the application of commercial labeling agents, such as fluorescent reagents, electron transfer dyes, radioactive isotopes, the color emitting quantum dot products of Quantum Dot Corp., gold, Nanogold, or other metallic labeling agents, as well as various labeling haptens such as amines, thiols, biotin, digoxygenin, dinitrophenol, FITC, etc., wherein such products may be attached to the reagents of the present invention including the modified poly-T primers, the various adapters and extenders and the ChipTAGs, GeneTAGs, TinkerTAGs, and reporter arrays thereof as previously described.

Oligonucleotide based expression arrays, such as the GENECHIPs of Affymetrix, Inc., have different capabilities and limitations relative to cDNA based chips. Reflecting these differences, oligonucleotide-based arrays are less suited for probes made primarily from the poly-A end of gene transcripts since such oligo-based arrays frequently target upstream as well as downstream gene regions and fail to score expression for a gene if all the oligonucleotides on the chip representing that gene do not show labeling. Therefore, the present invention alternatively provides methods to generate probes that better represent the entire gene transcript. The principle of this approach is to copy all or most of the entire transcripts, fragment the cDNA copies to make multiple probe fragments, and then use the methods and compositions developed and described here to append universal linkers to all the fragments so that the fragment set can be globally amplified and applied to expression arrays.

The present invention thus relates to a method for gene expression analysis that is devised for oligonucleotide-based arrays, called the Mini-WRAP-Probes method, wherein multiple double-linker probes are made from each transcript, the method comprising the steps of:
 a. making first strand cDNA probes from a RNA sample;
 b. fragmenting the probes with a fragmenting agent, the fragmenting agent selected from the group consisting of restriction enzymes, RNase, RNase-H, UNG, single stranded cutting enzymes, shearing, and sonication;
 c. applying a random probe modifier to the 3' end of the probe fragments to append a common universal linker, the random probe modifier selected from the group consisting of the random adapter composition and the random extender composition;
 d. polymerizing a second strand cDNA copy of the fragments with a primer comprising the universal linker sequence; and
 e. applying the random extender comprising the same universal linker sequence and the blocked 3' end to the probe fragments, wherein repeated thermal cycling is performed as described above to preferentially extend the 3' end of the second strand cDNA probe copies with a second universal linker sequence, to form double-linker probes from each probe fragment suitable for PCR amplification, labeling and application to expression assays, particularly oligonucleotide-based arrays.

Other embodiments of the Mini-WRAP-Probes methods employ these same procedures and reagents to create universal linkers on fragmented probes or fragmented DNA thus enabling either the amplification of the probes or fragments or the use of GeneTAGs and other reporters to increase probe signaling from small fragments.

One such application is the identification of small DNA fragments. DNA in preserved or frozen tissues, such as clinical, pathological or forensic specimens, are commonly degraded making it difficult to extract, amplify and identify the sequences. DNA fragments also appear in clinical specimens of blood and bodily fluids that are important indicators of disease or cancer but are difficult to concentrate or identify. Identifying degraded DNA is a particularly acute problem in studying Ancient DNA samples such as Egyptian and Etruscan mummies or biological samples preserved in glaciers, bogs, amber, etc. The present invention provides additional modifications of the Mini-WRAP-Probe method to amplify and identify any DNA fragment or set of fragments, wherein the following steps are applied to make and analyze the sample:
 a. providing a sample of unknown DNA fragments;
 b. applying a random probe modifier to the 3' end of the fragments to append a common universal linker, the random probe modifier selected from the group consisting of the random adapter composition and the random extender composition;
 c. polymerizing a second strand cDNA copy of the fragments with a primer comprising the universal linker sequence;
 d. applying the random extender composition, further comprising the same universal linker sequence and the blocked 3' end, to the fragments with repeated thermal cycling to preferentially extend the 3' end of the second strand cDNA copies with a second universal linker sequence, to form double-linker fragments suitable for PCR amplification; and
 e. amplifying the fragments and sequencing them to determine their sequence identity.

In this method, the probe modifier used to append the first universal linker is less critical, since there is only one potential 3' target for each probe fragment. Thus for this first step, the random adapter is the simplest approach. However, once the second strand copies of the fragments are polymerized, the random extender composition provides an important advantage since it will favor extending a 3' end which lacks a universal linker. Once a universal linker has been applied to a 3' end, another random extender attempting to anneal to that end will preferential bind the universal linker end of the random extender to the matching universal linker sequence already there—thus inactivating that extender molecule for that cycle. Consequently, the random extender composition will preferentially apply only one universal linker to each 3' end.

Other embodiments of the Mini-WRAP-Probes methods enable improved sensitivity with tissue microarrays or RNA arrays, wherein a cDNA probe prepared for such applications are modified by the above methods to append universal linkers to the probes, wherein the steps to make the probes comprise the following steps:

a. providing a fragmented cDNA probe;
b. applying a random probe modifier to append a first universal linker to the 3' end of the fragments;
c. polymerizing a second strand cDNA copy of the fragments;
d. applying the random extender composition, further comprising the same universal linker sequence and the blocked 3' end, to the fragments with repeated thermal cycling to preferentially extend the 3' end of the second strand cDNA copies with a second universal linker sequence, to form double-linker probe fragments;
e. hybridizing the probes to an array of RNA targets;
f. hybridizing reporter units to the linkers of the probes, the reporter units selected from the group of linker-primer-reporter compositions, multi-linkers, and reporters, the reporter comprising linear segments of label DNA or joined polynucleotides with a single stranded universal linker end; and
g. detecting the reporter units to detect the RNA targets.

The purpose of this method is to maximize signaling by creating a fractured set of probes, each of which can be labeled internally during PCR amplification or by binding reporters to the universal linkers of the probes, wherein such reporters could include multi-linkers, GeneTAGs and GeneTAG arrays.

A very important need of molecular biology and drug discovery research is the necessity of determining the sequences at the 5' end of gene transcripts which are frequently under-represented or lost in common procedures (some of these procedures are called 5' RACE). Such information is needed to determine the functional full-length sequences of a gene for drug discovery and patenting issues. The present invention provides a modified Mini-WRAP-Probe method wherein the Random Extender and the Back-Tagging procedure are employed to find and duplicate the absolute 3' end of first strand cDNA copies of a specific gene, wherein the steps of this procedure comprise the steps of:

i) providing a set of mRNA transcripts wherein the 5' end of the gene of interest has been copied as first strand antisense cDNA by reverse transcriptase using a gene specific primer, wherein the gene specific primer additionally comprises a universal linker sequence and a capture moiety;
ii) capturing and purifying the first strand cDNA copies of the targeted transcript;
iii) applying the random extender composition with rapid thermal cycling to extend the 3' end of the cDNA product with a universal linker sequence, wherein a double-linker product is formed suitable for PCR amplification; and
iv) amplifying and sequencing the double-linker cDNA product to determine the sequences of the 5' end of the gene.

The practice of the present invention employs, unless otherwise indicated, conventional techniques of molecular biology, microbiology and recombinant DNA techniques, which are within the skill of the art. Such techniques are explained fully in the literature. See, e.g., Sambrook, J. et al., Molecular Cloning; A Laboratory Manual, Second Edition (1989); Oligonucleotide Synthesis (M. J. Gait, ed., 1984); Nucleic Acid Hybridization (B. D. Hames & S. J. Higgins, eds., 1984) A Practical Guide to Molecular Cloning (B. Perbal, 1984); and the series Methods in Enzymology (Academic Press, Inc.).

The synthesis of some of the probe and reporter components of the present invention may be accomplished by conventional polymerase chain reaction (PCR) process. The protocol for PCR is set forth in Saiki et al., Science 230: 1350 (1985) and U.S. Pat. Nos. 4,683,195 and 4,683,202. A PCR adapter-linker method is set forth in Saunders et al. (1990); Johnson (1990) and PCT 90/00434. Another PCR method employing a mixture of primers is described in Meltzer et al., Nature—Genetics, 1 (1): 24-28 (April 1992).

Probe and reporter components of the present invention are also synthesized by conventional methods on a commercially available automated DNA synthesizer, e.g. an Applied Biosystems (Foster City, Calif.) model 380B, 392 or 394 DNA/RNA synthesizer. Preferably, phosphoramidite chemistry is employed according to, e.g., Beaucage et al., Tetrahedron, 48:2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679. In preferred embodiments of the present invention, the probe has a nuclease resistant backbone. Many types of modified oligonucleotides are available that confer nuclease resistance, e.g. phosphorothioate, phosphorodithioate, phosphoramidate. For phosphorothioates, see, e.g., Stec et al., U.S. Pat. No. 5,151,510; Hirschbein, U.S. Pat. No. 5,166,387; or Bergot, U.S. Pat. No. 5,183,885. For phosphoramidates, see, e.g., Froehler et al., International application PCT/US90/03138. In some embodiments it may be desirable to employ P-chiral linkages, e.g., Stec et al, EPO 92301950.9.

In several embodiments of the present invention, modified oligonucleotides are synthesized with internal spacers, commonly composed of carbon chains, which separate different functional regions of the oligonucleotide. Generally, spacers derived from phosphoramidite precursors, such as the carbon chain Spacer Phosphoramidites C9 or C18 from Glen Research, Inc. (Sterling, Va.), are preferred so that the modified oligonucleotides of the invention can be conveniently synthesized with commercial automated DNA synthesizers, e.g. Applied Biosystems, Inc. (Foster City, Calif.) model 394.

Spacer length may vary significantly depending on the nature of the probe and primer sequence. Preferably, spacer moieties are synthesized using conventional phosphoramidite and/or hydrogen phosphonate chemistries. Several phosphoramidite or hydrogen phosphonate monomers suitable for use in the present invention are set forth in Newton et al., Nucleic Acid Research, 21:1155-1162 (1993); Griffin et al., J. Am. Chem. Sot., 114:7976-7982 (1992) Jaschke et al., Tetrahedron Letters, 34:301-304 (1992); Ma et al, International application PCT/CA92/00423; Zon et al., International application PCT/US90/06630; Durand et al., Nucleic Acids Research, 18:6353-6359 (1990); and Salunkhe et al., J. Am. Chem. Soc., 114:8768-8772 (1992).

There is extensive background literature relating to the selection of hybridization conditions, labeling procedures, and the like, which is applicable to the principles and practice of the present invention. See, e.g. Wallace et al. Nucleic Acids Research 6:3543-3557 (1979); Crothers et al., J. Mol. Biol. 9:1-9 (1964); Gotoh, Adv. Biophys. 16:1-52 (1983) Wetruer, Critical Reviews in Biochemistry and Molecular Biology 26:227-259 (1991); Breslauer et al., Proc. Natl. Acad. Sci. 83:374-3750 (1986); Wolf et al., Nucleic Acids Research, 15:2911-2926 (1987); McGraw et al., Biotechniques, 8:674-678 (1990).

Conditions for annealing DNA based probes to DNA or RNA targets are well known, e.g., Nucleic Acid Hybridization, A Practical Approach (B. D. Homes, eds.), IRL Press, Washington, D.C. (1985). In general, whether such annealing or hybridization takes place is influenced by the length of the probes and the test substances, the pH, the temperature, the concentration of mono- and divalent cations, the proportion of G and C nucleotides in the hybridizing region, the viscosity of the medium and the possible presence of denaturants. Such variables also influence the time required for hybridization. The preferred conditions will therefore depend upon the particular application. Such conditions, however, can be routinely determined without undue experimentation.

For the joining of Adapters to probes, the preferred linking agent is a ligase, such as T4 DNA ligase, using well-known procedures (Maniatis, T. in Molecular Cloning, Cold Spring Harbor Laboratory (1982)). Other DNA ligases are also suitable. T4 DNA ligase may also be used when the test substance is RNA [Engler, M. J. et al., The Enzymes, Vol. 15, pp. 16-17 (1982), Higgins, N. P. et al., Methods in Enzymology, Vol. 68, pp. 54-56 (1979)]. Ligases from thermophilic organisms, e.g. Tth DNA ligase, Gene, Vol. 109, pp. 1-11 (1991), New England Biolabs, (Beverly, Mass.), and Ampligase, Epcentre Technologies, Inc. (Madison, Wis.) are preferred, so that ligation at higher temperatures may be carried out. The ligation, however, need not be an enzyme and, accordingly, the linking agent may be a chemical agent which will cause the probe components to link together. The invention is described using T4 DNA ligase as the linking agent. This enzyme requires the presence of a phosphate group on the 5' end of one polynucleotide and a 3' OH group on the neighboring polynucleotide.

For covalent joining of probe or reporter components of the present invention, the preferred cross linking agent is a bi- or tri-functional psoralen compound such as 4, 5', 8-trimethylpsoralen which intercalates the bases of hybridized DNA strands and causes covalent cross linking between them when treated with long wave ultraviolet to light, preferably in the range of 312 to 360 nanometers. Site specific cross-linking can also be facilitated by synthesizing an oligonucleotide probe component with a terminal psoralen molecule tethered by a carbon chain. Commercial reagents, such as C2 psoralen and C6 psoralen from Glen Research, Inc. (San Diego, Calif.), allow the termination of a synthetic oligonucleotide with an attached psoralen suitable for inducing crosslinking with double or triple strand configurations, respectively, using standard phosphoramidite chemistry on a automated DNA synthesizer, e.g. Applied Biosystems, Inc. (Foster City, Calif.) model 394. The durability of complementary hybridization between probe and reporter components may also be increased by employing artificial nucleotides; e.g. pdC-CE, pdU-CE, 5-Me-dC, Glen Research, Inc. (Sterling, Va.), which can significantly raise melt temperature (Tm) by several degrees, and can diminish non-specific binding of these components.

The probe and reporter molecules of this invention can be labeled during PCR amplification in the presence of appropriately modified dNTPs, or they can be labeled after completion of the PCR reaction by chemical or enzymatic modification of the PCR products. When the reporters are constructed of synthetic oligonucleotides, they can be labeled directly or indirectly by incorporating modified bases that either carry labeling agents or provide chemical or immunological means for the attachment of labeling agents. Alternatively, such reporters may contain secondary linkers for binding short oligonucleotides that are conjugated to labeling agents—usually at one end.

Any of the various labeling techniques, direct or indirect, may be used to label probes or reporters, including but not limited to fluorescent chemicals, radioactive materials, chemical haptens, or enzymatic modifiers. More than one label can be used. Preferred modified dNTPs include but are not limited to Cy3 or Cy5 labeled derivatives of dUTP or dCTP, biotin-16-dUTP; digoxigenin-1'-dUTP; biotin derivatives of dATP; fluoresceinated-dUTP; rhodamine labeled derivatives of dUTP or dCTP; hydroxy coumarin-labeled derivatives of dUTP; resorufin-11-2'-dUTP, and thiol or amine modified dNTPs, e.g. amino-allyl-dUTP, Sigma Chemical Co. (St. Louis, Mo.), Amino-Modifier C6-dT, Glen Research, Inc. (Sterling, Va.). Other potential labels that may be attached or conjugated to probe or reporter components include but are not limited to: (1) gold and silver particles; e.g. monomaleimido Nanogold, LI Silver, etc., to Nanoprobes, Inc., (Stony Brook, N.Y.); Colloidal Gold, Sigma Chemical Co. (Saint Louis, Mo.); (2) chemiluminescent or bioluminescent molecules such as aequorin, e.g. Aqualite, Sealite Sciences, Inc., (Norcross, Ga.); and (3) agents which can provide Raman spectrometry signaling such as DNA and histological dyes; e.g. Methyl green, Cresyl fast violet, Acridine orange, Ponceus S, Malachite green oxalate, Luxol fast blue, Cresyl violet acetate and Bromophenol blue; double and or triple bonded chemical labels; e.g. Chioracetonitrile, Propargyl chloride, 3'Methoxybenzyl chloride and alpha Bromo p-tolunitrile, Aldrich Chemical Company, Inc. (Milwaukee, Wis.); and propyne or methyl modified phosphoramidite nucleosides; e.g. pdC-CE, pdU-CE, 5-Me-dC, Glen Research, Inc. (Sterling, Va.). The staining intensity achieved with probes or reporters may be amplified with a variety of systems, including but not limited to fluorochrome conjugated avidin and/or labeled antibodies. Similarly, other known detection schemes such as labeling of probe molecules with enzymes, sulfur or mercury may be applied in order to suit special experimental conditions.

Methods for introducing oligonucleotide functionalizing reagents or to introduce one or more sulfhydryl, amino or hydroxyl moieties into probe or reporter sequences are described in U.S. Pat. No. 4,914,210. Such modified nucleotides can provide multiple signaling sites by incorporating them along the length of the probe or reporter molecule or at the ends of attached oligonucleotides. A 5' phosphate group can be introduced as a radioisotope by using polynucleotide kinase and gamma 32P-ATP to provide a reporter group. Biotin can be added to the 5' end by reacting an aminothymidine residue, or a 6-amino hexyl residue, introduced during synthesis, with an N-hydroxysuccinimide ester of biotin. Labels at the 3' terminus may employ polynucleotide terminal transferase to add the desired moiety, such as for example, cordycepin 35S-dATP, and biotinylated dUTP.

The present invention provides and contemplates the combination of the novel compositions of matters describe above, such as the Modified poly-T primers the various adapters and extenders, and the probe set compositions, wherein different variations may be created that are not specifically describe herein. These potential variations and combinations include modifications of the WRAP-Probe, Amplified-WRAP-Probe, and Mini-WRAP-Probe methods and their various manifestations thereof, with various GeneTAG, TinkerTAG or ChipTAG signal amplification systems. Alternatively, the compositions of matter and methods of the present invention are contemplated to be employed in combination with other commercial probe and signaling systems such as the dendrimers of Polyprobe, Inc. (Media, Pa.) [U.S. Pat. No. 5,487, 973] and the branch DNA (bDNA) components of Chiron Corp. (Emeryville, Calif.) [U.S. Pat. No. 5,124,246].

The probes and reporters of the present invention can be employed as diagnostic or drug discovery assays for a wide range of biomedical samples, including detection of nucleic acids and gene expression profiles in human diagnostics, forensics, and genomic analyses. See, e.g., Schena et al., Science, 270: 467-470 (1995); Schena, et al., Proc. Natl. Acad. Sci., 93:10614-9 (1996); Shalon et al., Genome Res., 6: 639-45 (1996); DeRisi et al., Nature Genetics, 14: 457-60, (1996); Heller et al., Proc. Natl. Acad. Sci., 94: 2150-5, (1997); Khan et al., Cancer Res., 58: 5009-13 (1998); Khan et al., Electrophoresis, 20: 223-9 (1999); Caskey, Science 236: 1223-1228 (1987); Landegren et al. Science, 242:229 237 (1988); and Amheim et al., Ann. Rev. Biochem., 61:131-156 (1992). Other diagnostic applications of the present invention include samples from the environment, e.g. from public water supplies, samples from foodstuffs, and from other biological or clinical samples, such as blood, saliva, lung sputum, semen, buccal smears, urine or fecal waste, cell and tissue biopsies and micro dissections, amniotic fluid, or tissue homogenates of plants, animals, or human patients, and the like.

The compositions and methods of the present invention can be readily employed in a variety of membrane formats such as expression macro and microarrays, dot blots, and Northern blots; in gels such as agar or polyacrylamide; in a variety of in situ formats to detect or map genes or RNA transcripts in sectioned tissue and tissue microarrays; in cultures or microwell plates to detect infectious microorganisms or unbound DNA fragments extracted from bodily fluids or wastes; and in various solid substrate chip formats that detect genes, mutations or mRNA expression levels, including but not limited to oligonucleotide microarrays, cDNA microarrays, and molecular detection chips employing fluorescence, radioactivity, optical interferometry, Raman spectometry or semi-conductor electronics.

EXAMPLES

Example 1

Sample Molecular Compositions of the Present Invention

Universal GeneTAG Linkers:
1. Red 5'CTACGATACGATAGCGCCTAAGAGTAG (Seq. ID. No. 1) and its complement.
2. Green 5'CCTAGACCTACGACATAGGTACCCTAC (Seq. ID. No. 2) and its complement.
3. Blue 5'CGTAGAACTAGCACGCTACGTACTAGG (Seq. ID. No. 3) and its complement.
4. Orange 5'GGCTATCGCTACGTAGACTAGACCTAC (Seq. ID. No. 4) and its complement.

Modified Poly-T Primer with red or green universal linker and anchor end:

```
                                          (Seq. ID. No. 1, 5)
1.   5'CTACGATACGATAGCGCCTAAGAGTAG-TTTTTTTTTTTT
     TTVN (Seq. ID. No. 2, 5)
2.   5'CCTAGACCTACGACATAGGTACCCTAC-TTTTTTTTTTTT
     TTVN
```

Double-Linker WRAP-Probe Set 1: Showing one probe strand with Red and Blue Universal Linkers, and with the variable target sequence indicated by S1 . . . Sn

```
                                          (Seq. ID. No. 1, 6)
     5'CTACGATACGATAGCGCCTAAGAGTAG-S1 . . . Sn-

CCTAGTACGTAGCGTGCTAGTTCTACG
```

Double-Linker WRAP-Probe Set 2: Showing one probe strand with Green and Orange Universal Linkers, and with the variable target sequence indicated by S1 . . . Sn

```
                                          (Seq. ID. No. 2, 7)
     5'CCTAGACCTACGACATAGGTACCCTAC-S1 . . . Sn-

GTAGGTCTAGTCTACGTAGCGATAGCC
```

Specific Adapter:

Version with Blue Universal Linker: a first polynucleotide with blue linker, an overhang specific to a restriction enzyme cut site (indicated by S1 . . . Sn), and a second complementary polynucleotide preferably 5' phosphorylated: (Seq. ID. No. 3, 6)

5'CGTAGAACTAGCACGCTACGTACTAGG-S1 . . . Sn
5'P-CCTAGTACGTAGCGTGCTAGTTCTACG

Version with Orange Universal Linker and label: (Seq. ID. No. 4, 7)

5'GGCTATCGCTACGTAGACTAGACCTAC-S1 . . . Sn
5'P-GTAGGTCTAGTCTACGTAGCGATAGCC-LABEL

Random Adapter Version with Blue Universal Linker: a first polynucleotide with blue linker, a random overhang sequence, typically of 2N's (indicated by N1 . . . Nn), and a second complementary polynucleotide preferably 5' phosphorylated:

```
                                          (Seq. ID. No. 3, 6)
     5'CGTAGAACTAGCACGCTACGTACTAGG-N1 . . . Nn

5'P-CCTAGTACGTAGCGTGCTAGTTCTACG
```

Random End-Linker (random extender): Version with Blue Universal Linker: Showing a polynucleotide with Blue linker sequences, a random overhang sequence, typically of 6 to 9N's (indicated by N1 . . . Nn), and a blocked 3' end. (Seq. ID. No. 3)

5'CTACGATACGATAGCGCCTAAGAGTAG-N1 . . . Nn-block

Homopolymeric Adapter Version with Blue Universal Linker: Showing a first polynucleotide with Blue linker sequences and a poly-C or poly-G sequence (indicated by C1 . . . Cn), and a second polynucleotide which is complementary to the first nucleotide and preferably 5' phosphorylated: (Seq. ID. No. 3, 6)

5'CGTAGAACTAGCACGCTACGTACTAGG-C1 . . . Cn
5'P-CCTAGTACGTAGCGTGCTAGTTCTACG

Homopolymeric extender: Version with Blue Universal Linker: Showing a polynucleotide with Blue linker sequences and a poly-C or poly-G sequence (indicated by C1 . . . Cn): (Seq. ID. No. 3)

5' CGTAGAACTAGCACGCTACGTACTAGG-C1 . . . Cn

Labeled ChipTAG Primers:
Red and Blue Linker/Primers with Cy5 fluor.

```
                                          (Seq. ID. No. 1)
     Red    5'-cy5-CTACGATACGATAGCGCCTAAGAGTAG (Seq. ID. No. 3)
     Blue   5'-cy5-CGTAGAACTAGCACGCTACGTACTAGG
```

Green and Orange Linker/Primers with Cy3 fluor.

```
                                          (Seq. ID. No. 2)
     Green  5'-cy3-CCTAGACCTACGACATAGGTACCCTAC (Seq. ID. No. 4)
     Orange 5'-cy3-GGCTATCGCTACGTAGACTAGACCTAC
```

Example 2

One-Linker WRAP-Probe Method

Total RNA is extracted from A549 lung cancer cells by standard methods. Reverse transcriptase (RT) is then employed to copy the mRNA transcripts to cDNA using a Modified poly-T Primer known as R-GT-RTP (Seq. ID. No. 8) having a 3' end of 15 poly-T's and a 5' end with a universal linker sequence that is similar to but differing in part from the Red Universal Linker of Example 1. For a comparative sample an alternative Modified poly-T Primer, known as G-GT-RTP (Seq. ID. No. 9) is used for the RT reaction to provide a second universal linker sequence wherein those sequences are also similar to but differing in part from the Green universal linker of Example 1.

The Examples 2 through 7 use these earlier versions of the red and green universal linkers in all their products, and thus the text of those Examples identifies them differently with the terms First-RED and First-GREEN in the descriptions to identify these sequence differences.

For a 25 ul reaction, 40 micrograms of A549 RNA was combined with 2 ul of 100 picomol/ul R-GT-RTP (Seq. ID. No. 8), 10×PCR buffer II, 25 mm MgCl2, 1 ul each of 10 mM dATP, dGTP and dTTP, 6 ul of 1 mM dCTP, 3 ml of 1 mM Cy3 dCTP (AP Biotech), and dH2O, and the mixture was placed in a 70 degrees C. waterbath for 10 min and allowed to cool at room temperature for 5 min. Then 50 units of MuVL reverse transcriptase enzyme (Perkin Elmer) was added along with 20 units of RNase inhibitor (Perkin Elmer) and the mixture was incubated at 42 degrees C. for 1 hour. The product was purified with a Centri-Sep spin column (Princeton Separations).

Type I GeneTAGs with a First-RED linker on the proximal end and Type II GeneTAGs with a First-GREEN linker on the proximal end were made and both types were labeled "red" with Cy5-dCTP by PCR amplification of an arbitrary MTB template, 600 bp long, using 2 ul of 0.25 ug/ul of template. The primers employed for Type I GeneTAGs are RR-SPC-F (SEQ ID NO. 10, 11) and GR-SPC-R: (SEQ ID NO. 12, 13) using 2 ul each at 10 pmol/ul. The primers employed for Type II GeneTAGs are GR-SPC-F: (SEQ ID NO. 14, 11) and RR-SPC-R: (SEQ ID NO. 15, 13) using 2 ul each at 10 pmol/ul. The internal spacers are identified as 99 indicating two C9 phosphoramidite spacers (Glen Research). Fluorescent labeling is accomplished during PCR amplification of the reporters wherein nucleotides are added with low dCTP (6 ul of 1 mM) plus normal dATP, dTTP and dGTP (1 ul each of 10 mM) plus 3 ul of 25 uM Cy5-dCTP. Taq, 10× buffer and dist. H2O were added and the mixture cycled 40 times at 94 degrees C., 55 degrees C. and 72 degrees C. for about 1 min per step. The products were purified twice with a Centri-Sep spin column.

The probes were hybridized overnight at 65 degrees C. to cDNA chips arrayed on poly-L-lysine coated glass slides with a Genetic Microsystems spotter using 5 ul of probe mixed with 7 ul of hybridization buffer, said buffer consisting of 3.5×SSC and 0.2% SDS and containing Cot 1 DNA, poly-A RNA, and tRNA. Each gene location on these chips are duplicated 5 times in vertical columns. After a brief wash with hybridization buffer, GeneTAGs were hybridized for an additional 2 hours under the same conditions. The chips were gently washed for 5 min each in three steps: 1) 2×SSC, 0.1% SDS, 2) 1×SSC, and 3) 0.1×SSC.

```
GeneTAG Modified Poly-T Primers:
a) First-RED Linker version R-GT-RTP
                                    (Seq. ID. No. 8)
5' CTACGATACGATAGGGCCTAAGAGTAG-TTTTTTTTTTTTTTT b) First-GREEN Linker version G-GT-RTP
                                    (Seq. ID. No. 9)
5' GCCTAGACCTAGGGGTAGCTAGGCTAC-TTTTTTTTTTTTTTT Type I GeneTAG Spacer Oligomers:
a) Proximal Spacer Oligomer RR-SPC-F:
                                    (SEQ ID NO. 10, 11)
5' CTACTCTTAGGCCCTATCGTATCGTAG-
   -99--CCAGGGTTTTCCCAGTCACGAC b) Distal Spacer Oligomer GR-SPC-R:
                                    (SEQ ID NO. 12, 13)
5' GCCTAGACCTAGGGGTAGCTAGGCTAC-
   -99--GAGCGGATAACAATTTCACACAGG Type II GeneTAG Spacer Oligomers:
a) Proximal Spacer Oligomer GR-SPC-F:
                                    (SEQ ID NO. 14, 11)
5' GTAGCCTAGCTACCCCTAGGTCTAGGC-
   -99--CCAGGGTTTTCCCAGTCACGAC b) Distal Spacer Oligomer RR-SPC-R:
                                    (SEQ ID NO. 15, 13)
5' CTACGATACGATAGGGCCTAAGAGTAG-
   -99--GAGCGGATAACAATTTCACACAGG
```

Figure 6A:
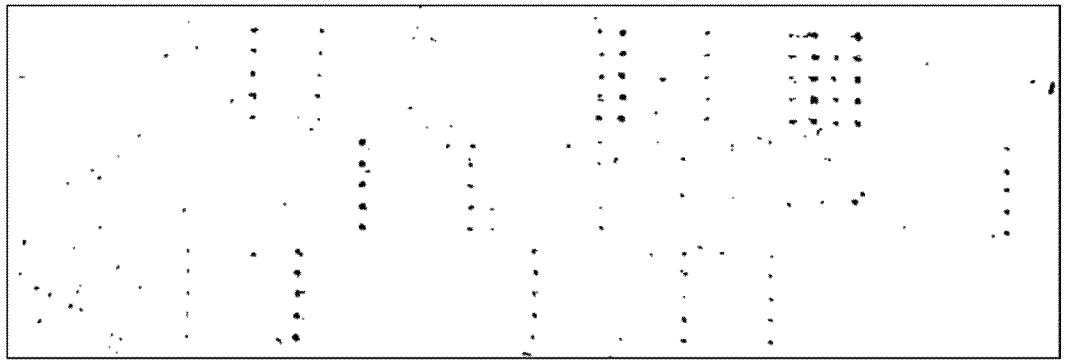
FIGS. 6A-6B: Images from Example 2.
Figure 6B:
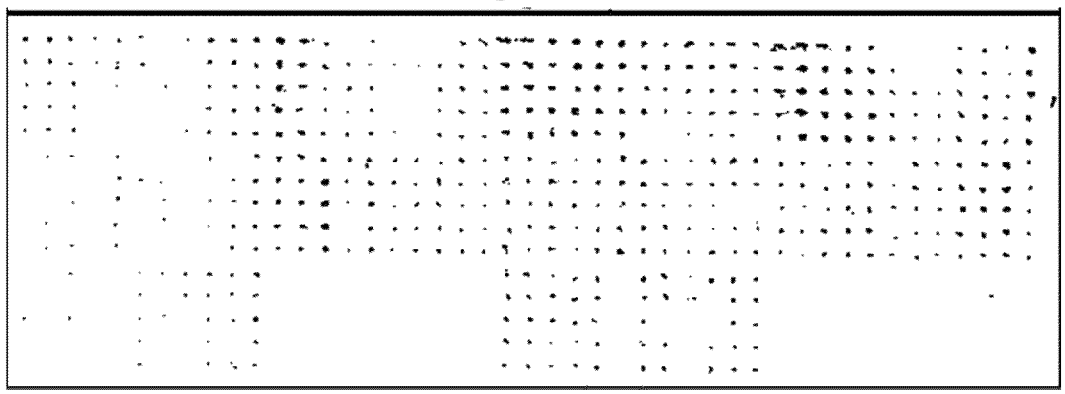

The chips are scanned with a Genetic Microsystems laser scanner and produce two gene expression profiles from the "green" channel and the "red" channel showing, respectively, differential signaling with both the labeled probes and with the labeled GeneTAGs bound to the probes. Since each gene target arrayed on these chips is duplicated in vertical columns five times, it is easy to see and confirm true differences in gene expression between genes. Approximately 20 gene locations on the chip show highly significant "green" labeling indicating specific gene expression levels for these cells, and approximately 200 gene locations showed significant "red" labeling indicating additional gene expression labeling provided by the GeneTAGs bound to the probes. Labeling intensity varies per each vertical set of gene targets for both the green and red channels indicating gene expression monitoring. See FIGS. 6A and B.

Example 3

Double-Linker WRAP-Probe Method with Restriction Cutting and Adapter Ligation Total RNA was extracted from A549 lung cancer cells by standard methods. A 40 ug sample was treated with reverse transcriptase (RT) and a Modified Poly-T Primer to make ds cDNA copies of the mRNAs with a first linker, to cut and capture the end fragments, and to add a second linker by ligating an adapter. The following steps were employed to make the probes and perform a chip analysis:

1. Full length first strand cDNAs were made with one hour exposure to MuVL RT (Gibco) at 37 degrees C. using a Modified Poly-T Primer (Seq. ID. No. 16) having a 5' biotin capture moiety, an overlap linker sequence and a poly-T segment. Nucleotides including Cy3-dCTP (AP Biotech) were incorporated as described above to provide "green" labeling.

2. Double stranded cDNA was made with E. coli DNA polymerase I, Rnase H and DNA ligase (Gibco kit) with a two hour exposure at 16 degrees C.

3. The ds cDNAs were treated with the restriction enzyme Nla III (New England Nuclear) for 7 hours at 37 degrees C. and purified twice with Centi-Sep spin columns.

4. The end fragments were captured with 10 mg strepavidin-coated magnetic beads (Dynal).

5. A pre-annealed First-RED Specific Adapter (Seq. ID. No. 17, 18) was prepared and ligated to the fragments with T4 DNA ligase (Boehringer Mannheim) for 30 min. at 37 degrees C. providing a first 5' First-RED Linker sequence.

6. The adapter modified fragments were again captured on magnetic beads, denatured with 0.2 M NaOH, and the eluted probes retained and neutralized.

7a. In part of the sample, a two part overlap linker (Seq. ID. No. 19) was annealed and cross linked to the ss probes to form a second 5' First-RED-Linker. Such probes are double-linker WRAP probes.

7b. Another part of the sample was instead used as templates for amplifying and labeling the probes by PCR. In this case, amplification was initially accomplished with a set of primers consisting of a first primer, which is the First-RED version of GeneTAG Modified Poly-T Primer used above (Seq. ID. No. 8), (this binds to the poly-A segment of the sense cDNA), and of a second primer, which is the First-RED Linker-primer (Seq. ID. No. 20) which contains the same sequences as the 5' end of the first primer. PCR is conducted for 10 cycles at 94 degrees 30', 48 degrees 30' and 72 degrees 45'. Then PCR amplification is repeated for 30 cycles using only the GeneTAG First-RED primer. Alternatively, in step 5 above a pre-annealed First-GREEN Specific Adapter (Seq. ID. No. 21, 22) could be employed for ligation to the cut sites, and thus, the resulting probes could be PCR amplified with the First-GREEN Modified Poly-T Primer (Seq. ID. No. 9). and a First-GREEN primer (Seq. ID. No. 23) in the same manner as described above using the First-RED compositions. Furthermore, the above GeneTAG First-GREEN or First-RED compositions could be employed together such that one primer would employ the First-GREEN linker/primer sequence and the other would employ the First-RED linker/primer sequence.

The resulting WRAP-Probes from step 7b. above were hybridized to cDNA chips overnight and then treated for 2 hours with Type III GeneTAGs previously labeled "red" with Cy5-dCTP (AP Biotech) as described in Example 2. Type III GeneTAGs have a proximal linker which binds to the First-RED Linker sequences of the WRAP-Probes and two distal linkers that bind to the proximal linker of Type IV GeneTAGs. The chips are washed once and then Type IV GeneTAGs are applied for two additional hours. The chips are then washed three times as described in Example 2 above. These chips are similarly prepared with vertical duplications of different gene targets, but in this case, four sets of targets vs. five sets of targets are represented in the vertical columns. The chips are scanned with a Genetic Microsystems scanner showing differential labeling with the probes and the GeneTAGs as described above. See FIGS. 7 and 8. This approach produces more extensive labeling with two layers of GeneTAGs.

```
GeneTAG Components:
Modified RT primer
                                        (Seq. ID. No. 16)
5' biotin-CGACTACCTATCTAC-TTTTTTTTTTTTTT First-RED GeneTAG Adapter part 1:
                                        (Seq. ID. No. 17)
5' CTACGATACGATAGGGCCTAAGAGTAG-CATG First-RED GeneTAG Adapter part 2:
                                        (Seq. ID. No. 18)
5' CTACTCTTAGGCCCTATCGTATCGTAG
```

```
-continued
Overlap Linker
                                        (Seq. ID. No. 19)
5' CTACGATACGATAGGGCCTAAGAGTAG-CGACTACCTATCTAC GeneTAG First-RED Primer:
                                        (Seq. ID. No. 20)
5' CTACGATACGATAGGGCCTAAGAGTAG First-GREEN Specific Adapter part 1:
                                        (Seq. ID. No. 21)
5' GCCTAGACCTAGGGGTAGCTAGGCTAC-CATG First-GREEN Specific Adapter part 2:
                                        (Seq. ID. No. 22)
5' GTAGCCTAGCTACCCCTAGGTCTAGGC GeneTAG First-GREEN Primer:
                                        (Seq. ID. No. 23)
5' GCCTAGACCTAGGGGTAGCTAGGCTAC b) First-GREEN Linker version G-GT-RTP
                                        (Seq. ID. No. 9)
5' GCCTAGACCTAGGGGTAGCTAGGCTAC-TTTTTTTTTTTTTTT Type III GeneTAGSpacer Oligomers:
a) Proximal Spacer Oligomer RR-SPC-F:
                                        (SEQ ID NO. 10, 11)
5' CTACTCTTAGGCCCTATCGTATCGTAG-
--99--CCAGGGTTTTCCCAGTCACGAC b) Distal Spacer Oligomer GR-SPC-R:
                                        (SEQ ID NO. 12, 12, 13)
5' GCCTAGACCTAGGGGTAGCTAGGCTAC-
-GCCTAGACCTAGGGGTAGCTAGGCTAC-
--99--GAGCGGATAACAATTTCACACAGG Type IV GeneTAG Spacer Oligomers:
a) Proximal Spacer Oligomer GR-SPC-F:
                                        (SEQ ID NO. 14, 11)
5' GTAGCCTAGCTACCCCTAGGTCTAGGC-
--99--CCAGGGTTTTCCCAGTCACGAC b) Distal Spacer Oligomer RR-SPC-R:
                                        (SEQ ID NO. 15, 15, 13)
5' CTACGATACGATAGGGCCTAAGAGTAG-
-CTACGATACGATAGGGCCTAAGAGTAG-
--99--GAGCGGATAACAATTTCACACAGG
```

Example 4

WRAP-Probe Method with Restriction Cutting, Adapter Ligation and ChipTAG Labeling A 10 microliter probe sample from Step 7b. of Example 3 above was re-amplified by PCR and applied to chips as described in Examples 2 and 3 above. However, in this case the First-RED ChipTAG primer (Seq. ID. No. 24) was employed as a single primer to globally amplify all probe products. Furthermore, internal labeling was not employed, and thus bound labeling was achieved from a single Cy5 fluor being attached to the 5' end of each single stranded probe component. Additionally, after PCR and before hybridization was conducted, an additional 0.2 microliter aliquot of First-RED ChipTAG primer at a concentration of 100 picomoles/microliter was added to the sample of purified probes. Since these added primers are labeled and they are capable of binding to the 3' linker end of each bound probe, they can provide additional signaling per probe. For two color comparisons, an additional ChipTAG with the First-GREEN sequences (Seq. ID. No. 25) can be employed to provide PCR amplified probes with a single Cy3 label per amplified product. These chips also used vertical duplications of the gene targets arrayed, and in this case, four duplications were again employed for each column of targets. See FIG. 9.

```
First-RED ChipTAG Primer
                                (Seq. ID. No. 24)
5' Cy5-CTACGATACGATAGGGCCTAAGAGTAG First-GREEN ChipTAG Primer
                                (Seq. ID. No. 25)
5' Cy3-GCCTAGACCTAGGGGTAGCTAGGCTAC
```

Example 5

WRAP-Probe Method with Short RT and Random End-Linker

Step 1: Samples of poly-A mRNA from mouse liver of controls and ANT-1 knockouts were employed to prepare probes for expression microarrays or chips. In each case 50 nanograms of poly-A mRNA were treated with GeneTAG RT primers in a brief RT reaction of 30 seconds using 1 ug of G-GT-RTP at 100 pmol/ul added to a 20 ul reaction. These RT reactions used Superscript II RT and 5×RT buffer (Gibco kit), dNTPs, and 0.1 M DTT and no labeling reagents. First the template and primer were combined in H2O for 5 min at 72 degrees C. and then placed on ice for 10 min. Thereafter, the enzyme, buffer, dNTPs and DTT were added, maintained at 42 degrees C. for 30 sec, and the reaction was stopped again on ice. The product was treated for 15 min at 75 degrees C. to inactivate the enzyme. The products were purified by Centri-Sep spin columns. This sub-procedure adds a first linker/primer site to the 5' ends of the cDNA probes and terminates RT copying prematurely to normalize the lengths of the probes.

Step 2: The above Control and ANT-1 samples were added to separate 30 ul reactions containing 100 picomoles of the First-GREEN version GeneTAG Random End-Linker (Seq. ID. No. 26), plus 10×PCR buffer, dNTPs, Taq polymerase and dH2O. The GeneTAG End-Linkers are 3' modified to prevent forward copying. Because of this modification, they are only effective in this reaction if they bind partially to the 3' end of the probes via the random segment and serve as a template to back extend the probes with a GeneTAG linker/primer sequence. PCR thermal cycling is then performed at 94 degrees C. for 10 sec, 42 degrees C. for 30 sec, and 72 degrees for 10 sec, for a total of 198 cycles. The products are purified with spin columns. This sub-procedure commonly extends the 3' ends of the probes with the First-GREEN GeneTAG linker sequence providing a second linker/primer site. In alternate preparations, the First-RED version GeneTAG End-Linker (Seq. ID. No. 27) is employed to put a First-RED GeneTAG linker sequence on the 3' end. The N's listed in to the End-Linker sequences below indicate bases which are randomly incorporated during oligonucleotide synthesis as either A, T, G, or C.

Step 3: The above Control and ANT-1 samples are again subjected to PCR cycling, but this time with conditions allowing the exponential amplification and labeling of the probes using the double-linker sites as primer sites. The samples are added to 100 ul PCR reactions containing 100 picomoles of the GeneTAG First-GREEN primer (Seq. ID. No. 23), 10×PCR buffer, Taq polymerase, and 16 ul of a mix of dNTPs with amino-allyl dUTP (Sigma) [wherein the stock mix contains 4 ul 100 mM AA-dUTP, 6 ul 100 mM dTTP, 10 ul 100 mM dATP, 10 ul 100 mM dCTP, 10 ul 100 mM dGTP and 760 ul dH2O]. PCR thermal-cycling is performed at 94 degrees C. for 30 sec, 48 degrees C. for 1 min, and 72 degrees for 30 sec, for a total of 40 cycles.

The probes are purified with Microcon-30 columns and dried in a SpeedVAC. The amino-conjugated bases of the Control probes are then coupled to Cy3 dye and the amino-conjugated bases of the ANT-1 probes are coupled to Cy5 dye using Cy3 or Cy5 monofunctional reactive dye packs from APBiotech. Before mixing the samples, the reactions are quenched with hydroxylamine to prevent cross coupling. Unincorporated or quenched Cy dyes are removed by purification with QiaQuick columns (Qiagen) and the labeled probes are concentrated by drying with a SpeedVAC. The probes were combined and one fifth the resulting sample was hybridized to mouse expression microarrays at 65 degrees C. for 16 hrs in 3.5×SSC plus 2% SDS and washed as described above. This sampling is essentially equivalent to starting with 10 nanograms of poly-A mRNA per sample. This procedure gave very short probes with limited chip signaling suggesting the need to reduce hybridization temperature and increase RT timing.

```
"First-GREEN" GeneTAG Random End-Linker
                                (Seq. ID. No. 26)
5' GCCTAGACCTAGGGGTAGCTAGGCTAC--NNNNNNNNNN--99

"First-RED" GeneTAG Random End-Linker
                                (Seq. ID. No. 27)
5' CTACGATACGATAGGGCCTAAGAGTAG--NNNNNNNNNN--99
```

Example 6

WRAP-Probe Method with Short RT and Random End-Linker (Membrane Arrays)

The Short RT and Random End-Linker method was more effective with longer RT extension periods. The following examples were prepared from experiments with human monocytes (derived from Red Cross buffy coat preps) to compare Control monocytes and IL-13 Treated monocytes.

Step 1: Essentially the same procedures from Step 1 of Example 5 above were employed except that the starting samples consisted of 1 microgram of total RNA per sample and the RT reaction for the Control RNA used the First-GREEN Modified Poly-T Primer (Seq. ID. No. 9) while the RT reaction for the IL-13 Treated RNA used the First-RED Modified Poly-T Primer (Seq. ID. No. 8). The RT reactions of 20 microliters contained 100 picomoles of GeneTAG Modified Poly-T Primer, 1 ul RT enzyme (SuperScript II) and 4 ul 5× buffer (Gibco kit), 1 ul dNTPs, 2 ul 0.1 M DTT and dH2O. The primers and RNA templates were mixed at 72 degrees C. for 5 min, and then the enzyme and other components were added and maintained at 42 degrees C. for various Short RT times of either 2, 5, 10 or 20 minutes, followed by 75 degree C. treatment for 15 min to stop the cDNA copying reaction prematurely from all transcripts regardless of gene specific differences in transcript length. The products were purified with Bio-Spin P-30 chromatography columns (Bio-Rad).

Step 2: This multi-cycle step was performed essentially the same as in Example 5 above except that the Control samples employed the First-GREEN Random End-Linker (Seq. ID. No. 26) while the IL-13 Treated samples employed the First-RED Random End-Linker (Seq. ID. No. 27). Thus the Control probes would have First-GREEN linker/primer sites at both ends while the IL-13 Treated probes would have First-RED linker/primer sites at both ends.

Step 3: This step was performed essentially the same as in Example 5 above except that the probes from the 20 min Short RT procedure were labeled with P-32 dCTP vs. fluorescence, and furthermore, the Control probes were amplified by PCR using the GeneTAG First-GREEN primer (Seq. ID. No. 20), and the IL-13 Treated probes were PCR amplified with the GeneTAG First-RED primer (Seq. ID. No. 23). For 100 ul reactions, 30 ul of probe template was employed with 100 picomoles of First-GREEN or First-RED for a total of 30 PCR cycles. Both products were purified, counted and adjusted to yield probes with an activity of one million cpm/ml.

Nylon membranes were arrayed with 10 gene target samples that were arranged in vertical columns of five slot blots per column. Each membrane of approximately 6 by 10 cm duplicated this 10 gene array pattern twice in a side by side arrangement. Each dot contained 200 nanograms each of plasmid cDNA from 6 candidate and 4 control targets: candidates: 5-LO, 12-LO, FLAP, COX-1, COX-2,15-LO, controls: Leptin, TNF-alpha, yeast and h-Actin. The target samples were denatured with 0.1 N NaOH, neutralized with Tris-HCl buffer, and UV crosslinked. Membranes were pre-hybridized for 4 hours in rotating roller bottles with 20 ml of hybridization solution (Rapid-hyb buffer, Amersham Life Science). The labeled and amplified probes were then added for overnight hybridization at 48 degrees C. with the same solutions, and then they were washed sequentially with 2×SSC and 0.1% SDS for 15 min, 0.2×SSC for 15 min 2 times, and 0.1×SSC for 15 min also at 48 degrees C. Expression profiling was obtained by exposing x-ray film for 12 hours. The repeated patterns evident within membranes also differed slightly between control and IL-13 treated monocytes, and as expected, IL-13 treatment up-regulated the expression activity of 15-LO. See FIG. 10.

Example 7

Amplified WRAP-Probe Method with Short RT and Random Adapter (on Membrane Arrays)

The same samples prepared for Example 6 above were also employed for an alternate method of attaching the second linker/primer sequence with a ligated GeneTAG Adapter. In these experiments, the PCR extension time was also increased from 30 sec to 1.5 min to allow more representation of the longer RT products in the sample of amplified probes. This change also shifts the sampling that will appear on the chip. Since all prior methods for expression microarrays are biased in signaling relative to probe length, further study is needed to determine which profiling pattern will prove to be more accurate.

Step 1: Essentially the same procedures from Step 1 of Example 6 were employed with starting samples consisting of 1 microgram of total RNA per sample. All samples were from monocyte controls and the RT reactions used the First-GREEN Modified Poly-T Primer (Seq. ID. No. 9) to produce the first linker/primer site. Alternatively, the First-RED Modified Poly-T Primer (Seq. ID. No. 8) could be employed for other comparisons. Short RT was conducted as described above with reduced RT exposure times of 2, 5, 10 or 20 minutes.

Step 2: This step was performed quite differently from that of Example 4 above since, in this case, the second linker/primer site was affixed to the 3' ends of the probes by direct ligation of First-GREEN Random Adapters. These random Adapters are composed of two oligonucleotides that are annealed together and of which one component provides a two base overhang of random sequences. These Random Adapters consist of a first oligonucleotide with First-GREEN linker sequences on the 5' end and two N's on the 3' end (Seq. ID. No. 28), and of a second oligonucleotide. (Seq. ID. No. 29) with sequences complementary to the First-GREEN linker sequences and with the 5' end phosphorylated during synthesis to facilitate ligation. In alternate preparations, a First-RED version of such Adapters could be employed which is made of a first oligonucleotide with First-RED linker sequences on the 5' end and two N's on the 3' end (Seq. ID. No. 30), and of a second oligonucleotide (Seq. ID. No. 31) with sequences complementary to the First-RED linker sequences. For this preparation, the two Random Adapter oligonucleotides were mixed together at a concentration of 100 picomoles/ul per product and then annealed for 2 hours at 37 degrees C. with 10 percent 10×PCR buffer and dH2O. This product was chilled on ice and stored at −20 degrees C. Samples treated by Step 1 above were combined with said Random Adapters in a 30 ul reaction consisting of 20 ul of probe template, 1 ul of Adapter, then 2 ul of T4 ligase and 6 ul of 5× Ligation buffer (Gibco kit) and dH2O. This ligation was conducted at 16 degrees C. overnight, but alternatively could be accomplished at 37 degrees C. for one hour. This reaction joins the Random Adapter to the 3' end of the probes creating a second linker/primer site.

Step 3: The probes can be amplified and labeled by PCR with standard methods. However, in this case two stages of amplification were employed. First, a 100 ul reaction of 20 cycles is conducted with 10 ul of probe product (after Adapter ligation), 1 ul of First-GREEN Linker (Seq. ID. No. 23) at 100 pmols/ul, 10 ul of 10×PCR buffer, 8 ul of dNTPs, 1 ul of Taq polymerase and dH2O. Then 10 ul of the above reaction is again amplified in a second PCR reaction of 100 ul for 30 cycles using 5 ul of P-32 dCTP (NEN Dupont) plus 1 ul of 1 mM dCTP, and 1 ul each of 10 mM dATP, dTTP and dGTP. Both reactions are thermocycled at 94 degrees C. 30 sec, 55 degrees C. 1 min, and 72 degrees C. for 1.5 min. The probes are purified by Centri-Sep spin column and applied to the membranes as described in Example 5 using pre-hybridization, hybridization and washing as indicated above. This procedure labels the probes internally. See FIG. 11. These results show that 2 min, 5 min and 10 min Short RT yield effective and relatively similar probe products and expression profiles while 20 min Short RT yields a relatively weaker set of products.

```
First-GREEN Random Adapter part 1
                              (Seq. ID. No. 28)
5' GCCTAGACCTAGGGGTAGCTAGGCTAC--NN First-GREEN Random Adapter part 2
                              (Seq. ID. No. 29)
5' GTAGCCTAGCTACCCCTAGGTCTAGGC First-RED Random Adapter part 1
                              (Seq. ID. No. 30)
5' CTACGATACGATAGGGCCTAAGAGTAG--NN First-RED Random Adapter part 2
                              (Seq. ID. No. 31)
5' CTACTCTTAGGCCCTATCGTATCGTAG
```

Throughout this application, various publications may have been referenced. The disclosures of these publications in their entireties are hereby incorporated by reference into this application in order to more fully describe the state of the art to which this invention pertains.

The embodiments described above are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

What is claimed is:

1. A system to replicate or globally replicate one or more nucleic acid species in a sample, the system comprising:
   (a) a random extender unit comprising a polynucleotide with a 3' random primer sequence and a 5' first universal sequence; wherein the first universal sequence is not complementary to the target nucleic acid species in the sample, and wherein the first universal sequence is selected from the group consisting of: SEQ ID NOs: 1, 2, 3 and 4, and wherein the 3' end of the population of random extender units is blocked, wherein said block is not thermally removable; and
   (b) a first universal primer comprising the first universal sequence.

2. The system of claim 1, further comprising: (i) a first population of polynucleotides comprising nucleic acid species in the sample that have been extended on their 3' ends with a sequence complementary to the first universal sequence, and (ii) a second population of polynucleotides comprising partial copies of the nucleic acid species in the sample that are extended on their 5' ends with the first universal sequence, wherein said 3' or 5' extended polynucleotides are generated by mixing the sample comprising the nucleic acid species with the random extender units, a DNA polymerase, and a reaction mix, wherein the random extender units hybridize to the nucleic acid species and thereby generate the 3' or 5' extended polynucleotide species by the DNA polymerase activity thereof.

3. The system of claim 2, further comprising copies of the first population of polynucleotides 3' or 5' extended on both ends with the universal sequence or its complement; wherein said copies are generated by mixing the population of 3' or 5' extended polynucleotides with a population of first universal primers, a DNA polymerase, and a reaction mix, wherein the extended polynucleotides and first universal primers hybridize together and generate extended copies thereof by the DNA polymerase activity.

4. The system of claim 3, further comprising a PCR reaction chamber providing repeated cycles of thermal denaturation, annealing and extension, wherein said extended full or partial copies of the nucleic acid species are amplified by the DNA polymerase activity thereof.

5. The system of claim 1, wherein the first universal primer is labeled.

6. The system of claim 3, wherein the reaction mix employed further comprises labeling components suitable for incorporation into the polynucleotide species or copies thereof.

7. The system of claim 1, further comprising an array comprising at least one probe complementary to a target nucleic acid species.

8. The system of claim 7, further comprising the amplified, labeled, extended copies of the nucleic acid species in the sample hybridized to the probes in the array; wherein the frequency of the target nucleic acid species in the sample is assessed by detecting the pattern of array labeling.

9. The system of claim 1, wherein the 3' primer sequence of the random extender unit comprises about 2 to about 15 nucleotides wherein each base position randomly comprises an A, T, G or C.

10. The system of claim 1, wherein each random extender unit further comprises a second polynucleotide complementary to the first universal sequence, and wherein the second polynucleotide is hybridized to the first universal sequence thereby generating a two part random extender unit.

11. The system of claim 10, wherein the two part random extender units are ligated to the target polynucleotide sequences.

12. The system of claim 1, wherein two or more random extender units, comprising different universal sequences, are separately joined to the target nucleotide sequences of two or more samples.

13. The system of claim 1, further comprising a poly-T universal primer, wherein the 3' end comprises about 10 to about 20 thymidines, and wherein the 5' end comprises a second universal sequence.

14. The system of claim 13, wherein the poly-T universal primer comprises a dinucleotide anchor sequence at the 3' end thereof, wherein the terminal base is A, T, G or C and the penultimate base is A, G or C, but not T.

15. The system of claim 13, further comprising a second universal primer complementary to the second universal sequence of the poly-T universal primer.

16. The system of claim 15, wherein the second universal primer is labeled.

17. The system of claim 13, wherein the second universal sequence is selected from the group consisting of: SEQ ID NOs: 1, 2, 3, and 4.

18. The system of claim 13, wherein the first and the second universal sequences are identical.

19. The system of claim 13, further comprising a population of the nucleic acid species in the sample or copies thereof that have been extended on their 3' ends with a sequence complementary to the first or second universal sequence, and extended on their 5' ends with the first or second universal sequence, wherein said population is suitable for global amplification and labeling and detection on an array comprising probes complementary to one or more target nucleotide species.

20. The system of claim 1, further comprising a GeneTAG reporter unit comprising (i) a multiply-labeled linear segment of double-stranded DNA and (ii) a terminal single stranded linker at one or both ends comprising a sequence complementary to the first or second universal sequence.

21. The system of claim 20, wherein the multiply-labeled DNA segment comprises about 100 to about 1000 base pairs.

22. A system to replicate or globally replicate and label one or more target nucleic acid species in a sample for array detection, the system comprising:

(a) a specific extender unit comprising two polynucleotides joined together: (i) a first oligonucleotide comprising a 5' universal sequence not complementary to the target nucleotide sequence and selected from the group consisting of: SEQ ID NOs: 1, 2, 3 or 4 and a 3' overhang sequence complementary to a restriction enzyme cut site, and (ii) a second polynucleotide comprising a sequence complementary to the universal sequence;

(b) a labeled universal primer comprising the universal sequence;

(c) a restriction enzyme specifically cleaving the restriction enzyme cut site;

(d) a sample comprising the target nucleic acid species fragmented with the restriction enzyme, wherein said fragments comprise a single stranded overhang complementary to the 3' overhang of the specific extender unit;

(e) an array comprising at least one probe complementary to a target nucleic acid sequence in the sample.

23. The system of claim 22, further comprising two or more restriction enzymes with different cut sites applied to the sample; and comprising two or more specific extender units wherein each specific extender is constructed with a 3' overhang sequence complementary to one of the restriction enzyme cut sites generated.

24. The system of claim 22, further comprising the specific extender units ligated to the fragmented nucleic acid species, and a DNA polymerase, and a reaction mix, and the labeled universal primer; wherein the DNA polymerase activity thereof generates an amplified labeled population of polynucleotides comprising copies of the nucleic acid species in the sample; wherein said polynucleotides are extended on one or both ends with the first universal sequence or its complement.

25. The system of claim 22, comprising said amplified labeled polynucleotides; and further comprising an array comprising at least one probe complementary to a target nucleic acid species; wherein the frequency of target nucleic acid species in the sample is assessed by hybridizing the amplified labeled polynucleotides to the array and detecting the pattern and intensity of labeling.

26. An extender and reporter system, to globally copy and multiply-label unknown mRNA transcripts in a sample, the system comprising:

(a) a poly-T universal primer, wherein the 3' end comprises about 10 to about 20 thymidines, and wherein the 5' end comprises a universal sequence not complementary to the target nucleic acid species in the sample and is selected from the group consisting of SEQ ID NOs: 1, 2, 3, and 4;

(b) a linear GeneTAG reporter unit comprising a multiply-labeled segment of double stranded DNA, about 100 to about 1000 base pairs long, and a single stranded linker at one or both ends that is complementary to the universal sequence;

(c) a sample comprising at least one mRNA transcript, wherein each transcript consists of a gene specific target nucleotide sequence and a 3' poly-A tail;

(d) a first mixture comprising the poly-T universal primer, the sample, a DNA polymerase and a reaction mix; wherein the polymerase activity generates DNA copies comprising the target nucleotide sequences and a 5' universal linker sequence;

(e) a second mixture comprising the DNA copies extended with the universal linker, the GeneTAG reporters, and a hybridization mix; wherein the extended DNA copies are hybridized to the GeneTAG reporters, generating DNA copies of the transcripts terminally joined to multiply-labeled linear reporters.

27. The system of claim 26, further comprising an array comprising one or more probes complementary to the target nucleotide sequences; wherein the extended DNA copies are hybridized to the linear reporters and to the array, either at the same time or separately; wherein array labeling is detected to measure the frequency of the targeted mRNA transcripts in the sample.

28. A method for detecting a target nucleic acid sequence of a biological sample, the method comprising the steps of:
    (a) providing mRNA transcripts from a biological sample;
    (b) generating a population of cDNA molecules from the mRNA transcripts, wherein the cDNA molecules each comprise a universal oligonucleotide linker at the 5' end of the poly-thymidine region, wherein the nucleotide sequence of the universal oligonucleotide linker is complementary to a nucleotide sequence of an oligonucleotide linked to a reporter molecule, and wherein the universal oligonucleotide linker has the nucleic acid sequence selected from the group consisting of: SEQ ID NOs: 1-4, and the complementary sequences thereof,
    (c) hybridizing the cDNA molecules to an array and contacting the array with a composition comprising a labeled reporter molecule, whereupon the reporter molecule binds to a universal oligonucleotide linker of a cDNA molecule, or optionally, contacting the cDNA molecules with a composition comprising a labeled reporter molecule, whereupon the reporter molecule binds to a universal oligonucleotide linker of a cDNA molecule and hybridizing the cDNA to an array; and
    (d) detecting the labeled reporter molecules, thereby detecting a target nucleic acid sequence in the biological sample.

29. The method of claim 28, wherein the step of generating a population of cDNA molecules from the mRNA transcripts comprises using at least one oligonucleotide primer comprising:
    (i) a poly-thymidine region; and
    (ii) a universal oligonucleotide linker at the 5' end of the poly-thymidine region, wherein the universal oligonucleotide linker has a nucleic acid sequence selected from the group consisting of: SEQ ID NOs: 1-4, and the complementary sequences thereof.

30. The method of claim 29, wherein the oligonucleotide primer sequence comprises between about 12 to about 20 thymidine bases, and the oligonucleotide primer further comprises a dinucleotide anchor sequence at the 3' end thereof, said anchor sequence comprising a 5' base selected from A, C, or G, and a terminal base selected from A, C, G, and T.

31. The method of claim 28, wherein the oligonucleotide primer comprises a capture moiety.

32. The method of claim 31, wherein the capture moiety is biotin.

33. The method of claim 28, wherein the step (b) further comprises using a random extender oligonucleotide to attach a universal oligonucleotide linker to the 3' end of the probes, wherein the random extender oligonucleotide comprises:

a universal oligonucleotide linker at the 5' end of the random extender oligonucleotide, wherein the universal oligonucleotide linker has the nucleic acid sequence selected from the group consisting of: SEQ ID NOs: 1-4, and the complementary sequences thereof; and
a variable nucleotide sequence of between about 4 to about 10 nucleotides extending from the 3' end of the universal oligonucleotide linker, wherein each base of the variable nucleotide sequence can be any of A, C, G, and T, and wherein the terminal 3' base of the said variable nucleotide sequence is optionally modified to prevent polymerase extension therefrom.

34. The method of claim 33, wherein the random extender oligonucleotide is attached to a cDNA probe by PCR cycling, thereby extending the 3' end of the cDNA probe with a universal oligonucleotide linker.

35. The method of claim 28, wherein the step (b) further comprises using an adapter duplex nucleic acid to append a universal oligonucleotide linker to the 3' end of the probes, wherein the adapter duplex nucleic acid, comprises:
    a first oligonucleotide strand comprising a universal oligonucleotide linker having a nucleic acid sequence selected from the group consisting of: SEQ ID NOs: 1-4, and the complementary sequences thereof; and
    a second oligonucleotide strand comprising a nucleotide sequence complementary to that of the first oligonucleotide strand;
wherein one of the first or second oligonucleotide strands has a single-stranded overhang.

36. The method of claim 35, wherein the single-stranded overhang is from 1 to about 6 nucleotides in length, wherein each base of the single-stranded extension is any of A, C, G, and T.

37. The method of claim 35, wherein the single-stranded overhang is complementary to a sequence cleavable by a restriction enzyme.

38. The method of claim 35, wherein the single-stranded overhang is a poly-guanine sequence or a poly-cytosine sequence.

39. The method of claim 35, wherein the adapter duplex nucleic acid is attached to a cDNA probe by ligation, thereby extending the 3' end of the cDNA probe with a universal oligonucleotide linker.

40. The method of claim 28, wherein the cDNA molecules generated by said method comprise a universal oligonucleotide linker, or complement thereof at both ends, and wherein step (b) of said method further comprises amplifying the cDNA molecules using primers, said primers selected to complement the universal oligonucleotide linker sequence, or a complement thereof, attached to the cDNA molecules.

41. The method of claim 40, wherein the primers comprise labeled reporter molecules.

42. The method of claim 41, wherein the reporter molecules comprise at least one terminal single stranded polynucleotide linker complementary to a universal oligonucleotide linker, and an attached reporter segment, wherein the reporter segment comprises a double stranded nucleic acid region and at least two labeling molecules attached thereto.

\* \* \* \* \*